(12) United States Patent
Cheng et al.

(10) Patent No.: US 11,124,605 B2
(45) Date of Patent: Sep. 21, 2021

(54) ANTIMICROBIAL ALPHA-HELICAL CATIONIC POLYPEPTIDES

(71) Applicant: The Board of Trustees of the University of Illinois, Urbana, IL (US)

(72) Inventors: Jianjun Cheng, Champaign, IL (US); Menghua Xiong, Urbana, IL (US); Ziyuan Song, Urbana, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 15/739,090

(22) PCT Filed: Jun. 27, 2016

(86) PCT No.: PCT/US2016/039657
§ 371 (c)(1),
(2) Date: Dec. 21, 2017

(87) PCT Pub. No.: WO2016/210442
PCT Pub. Date: Dec. 29, 2016

(65) Prior Publication Data
US 2018/0179336 A1 Jun. 28, 2018

Related U.S. Application Data

(60) Provisional application No. 62/185,345, filed on Jun. 26, 2015.

(51) Int. Cl.
| | |
|---|---|
| *C08G 69/48* | (2006.01) |
| *A61K 38/00* | (2006.01) |
| *A61K 31/43* | (2006.01) |
| *C08G 69/10* | (2006.01) |
| *A61K 31/496* | (2006.01) |
| *A61K 31/65* | (2006.01) |
| *A61K 31/7036* | (2006.01) |
| *A61P 31/04* | (2006.01) |
| *A01N 37/46* | (2006.01) |
| *A01N 43/40* | (2006.01) |
| *A01N 43/42* | (2006.01) |
| *A01N 43/50* | (2006.01) |
| *A01N 43/52* | (2006.01) |
| *A61K 31/785* | (2006.01) |
| *A61K 45/06* | (2006.01) |

(52) U.S. Cl.
CPC .............. *C08G 69/48* (2013.01); *A01N 37/46* (2013.01); *A01N 43/40* (2013.01); *A01N 43/42* (2013.01); *A01N 43/50* (2013.01); *A01N 43/52* (2013.01); *A61K 31/43* (2013.01); *A61K 31/496* (2013.01); *A61K 31/65* (2013.01); *A61K 31/7036* (2013.01); *A61K 31/785* (2013.01); *A61K 38/00* (2013.01); *A61K 45/06* (2013.01); *A61P 31/04* (2018.01); *C08G 69/10* (2013.01); *Y02A 50/30* (2018.01)

(58) Field of Classification Search
CPC ........ A01N 37/46; A01N 43/40; A01N 43/42; A01N 43/50; A01N 43/52; A61K 31/43; A61K 31/496; A61K 31/65; A61K 31/7036; A61K 31/785; A61K 38/00; A61K 45/06; A61P 31/04; C08G 69/10; C08G 69/48
See application file for complete search history.

(56) References Cited

U.S. PATENT DOCUMENTS

| | | | | |
|---|---|---|---|---|
| 5,962,410 | A | 10/1999 | Jaynes et al. | |
| 6,251,967 | B1 * | 6/2001 | Perichaud | ............. A01N 25/10 523/122 |
| 2003/0119754 | A1 * | 6/2003 | Lackey | ............... C07D 231/12 514/23 |
| 2006/0292135 | A1 * | 12/2006 | Loomis | .......... C12Y 403/01024 424/94.1 |
| 2010/0291672 | A1 | 11/2010 | Takeoka et al. | |
| 2013/0274173 | A1 * | 10/2013 | Cheng | .................... C08G 69/08 514/2.4 |

FOREIGN PATENT DOCUMENTS

| | | | | |
|---|---|---|---|---|
| JP | 63096200 | * | 4/1988 | ............. A61K 47/00 |

OTHER PUBLICATIONS

Bahar et al., "Antimicrobial Peptides," Pharmaceuticals, 6:1543-1575, Nov. 2013.
Brogden et al., "Will New Generations of Modified Antimicrobial Peptides Improve Their Potential as Pharmaceuticals?" Int. J. of Antimicrobial Agents, 38:217-225, May 2011
Brogden, "Antimicrobial Peptides: Pore Formers or Metabolic Inhibitors in Bacteria?" Nature, 3:238-250, Mar. 2005.
Chen et al., "Rational Design of α-Helical Antimicrobial Peptides with Enhanced Activities and Specificity/Therapeutic Index," J. Biol. Chem., 280(13):12316-12329, Apr. 2005.
Chin et al., "Biodegradable Broad-Spectrum Antimicrobial Polycarbonates: Investigating the Role of Chemical on Activity Structure and Selectivity," Macromolecules, 46(22):8797-8807, Nov. 2013.

(Continued)

*Primary Examiner* — Matthew P Coughlin
*Assistant Examiner* — Thurman Wheeler
(74) *Attorney, Agent, or Firm* — Haukaas Fortius PLLC; Michael H. Haukaas

(57) ABSTRACT

The invention provides antimicrobial polypeptides (AMPs) with high radial amphiphilicity. Unlike typical AMPs characterized by facial amphiphilicity or biomimetic antimicrobial polymers with randomly distributed charged and hydrophobic groups, these new AMPs are homo-polypeptides with radially amphiphilic structure. They adopt a stable α-helical conformation with a hydrophobic helical core and a charged exterior shell, formed by flexible hydrophobic side chains with terminal charge group. The radially amphiphilic polypeptides offer several advantages over conventional AMPs with regard to stability against protease and simplicity of design. They also exhibit high antibacterial activity against both Gram-negative and Gram-positive bacteria and low hemolytic activity. The AMPs thus provide a general platform for treating drug-resistant bacterial infections.

14 Claims, 13 Drawing Sheets

(56) References Cited

OTHER PUBLICATIONS

Engler et al., "Effects of Side Group Functionality and Molecular Weight on the Activity of Synthetic Antimicrobial Polypeptides," Biomacromolecules, 12(5):1666-1674, May 2011.
Gabrielson et al., "Reactive and Bioactive Cationic a-Helical Polypeptide Template for Nonviral Gene Delivery," Agnew. Chem. Int. Ed., 51:1143-1147, Jan. 2012.
International Search Report and Written Opinion of the ISA/US dated Sep. 22, 2016 in International Application No. PCT/US2016/039657; 6pgs.
Lee et al., "Two Interdependent Mechanisms of Antimicrobial Activity Allow for Efficient Killing in Nylon-3-Based Polymeric Mimics of Innate Immunity Peptides," Biochimica et Biophysica Acta, 1838:2269-2279, Sep. 2014.
Lu et al., " Ionic Polypeptides with Unusual Helical Stability" Nat Commun., 2(206):1-9, Feb. 2011.
Lu et al., "Hexamethyldisilazane-Mediated Controlled Polymerization of r-Amino Acid N-Carboxyanhydrides," J. Am. Chem. Soc., 129(46):14114-14115, Oct. 2007.
Ng et al., "Synergistic Co-Delivery of Membrane-Disrupting Polymers with Commercial Antibiotics against Highly Opportunistic Bacteria," Adv Mater., 25(46):6730-6736, Dec. 2013.
Raguse et al., "Structure-Activity Studies of 14-Helical Antimicrobial P-Peptides: Probing the Relationship between Conformational Stability and Antimicrobial Potency," J Am Chem Soc, 124(43):12774-12785, Oct. 2002.
Schmidt et al., "Criterion for Amino Acid Composition of Defensins and Antimicrobial Peptides Based on Geometry of Membrane Destabilization," J. Am. Chem. Soc., 133:6720-6727, May 2011.
Tejero et al., "High Efficiency Antimicrobial Thiazolium and Triazolium Side-Chain Polymethacrylates Obtained by Controlled Alkylation of the Corresponding Azole Derivatives," Biomacromolecules., 16(6):1844-1854, Jun. 2015.
Xiong et al., "Helical Antimicrobial Polypeptides with Radial Amphiphilicity," Proc Natl Acad Sci U S A., 112 (43):13155-13160, Oct. 2015 (with Supporting Information, pp. 35).
Yang et al., "Synthetic Antimicrobial Oligomers Induce a Composition-Dependent Topological Transition in Membranes," J Am Chem Soc., 129(40):12141-12147, Oct. 2007.
Yin et al., "Supramolecular Self-Assembled Nanoparticles Mediate Oral Delivery of Therapeutic TNF-a siRNA against Systemic Inflammation," Angew. Chem. Int. Ed., 52(22):5757-5761, May 2013.
Matsumoto et al., "Preparation and Properties of Phospholipid-Modified Polypeptide," Macromolecules, 29 (7):2372-2377, Mar. 1996.

* cited by examiner

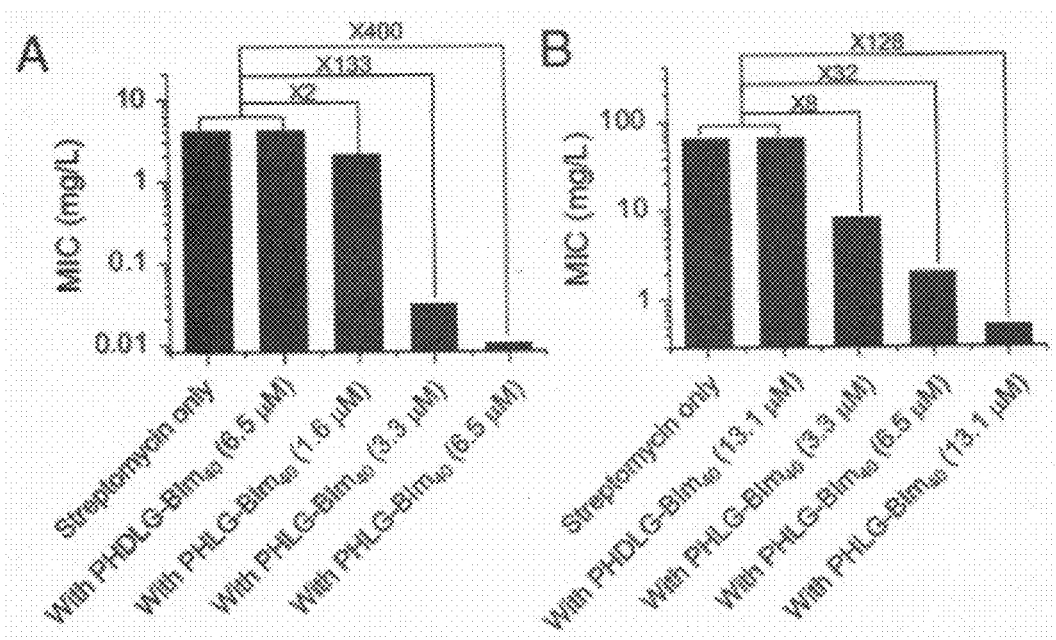
Fig. 4A-B
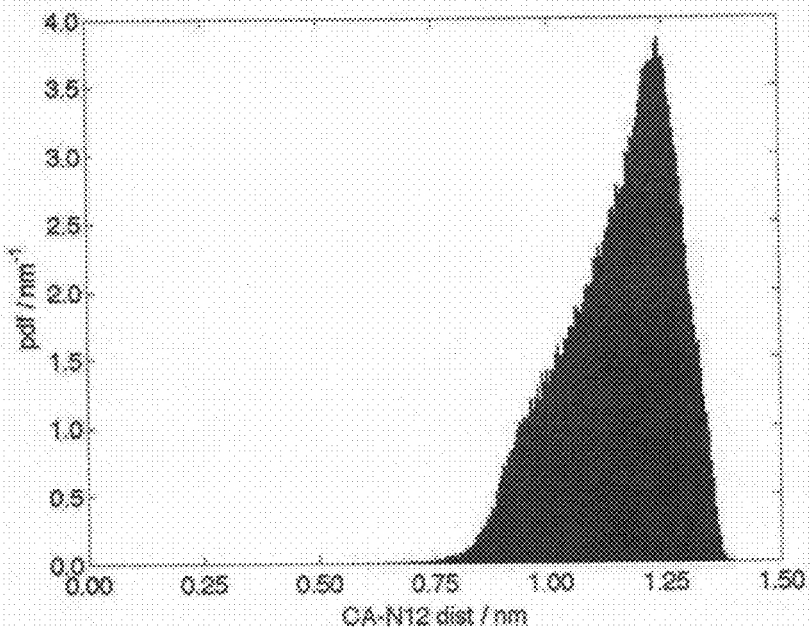
Fig. 5

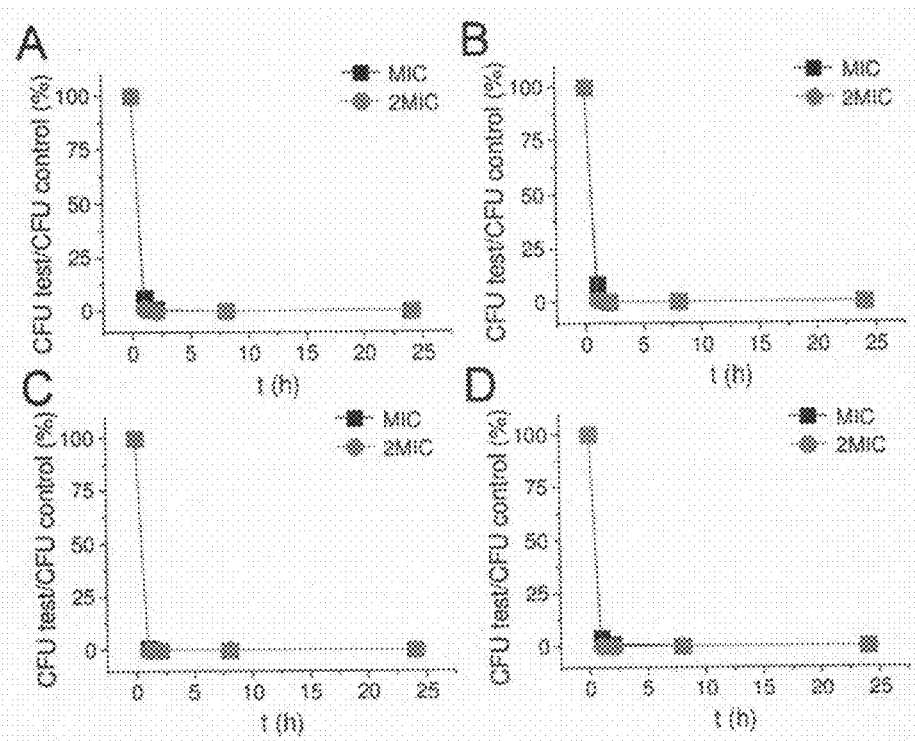
Fig. 6A-D
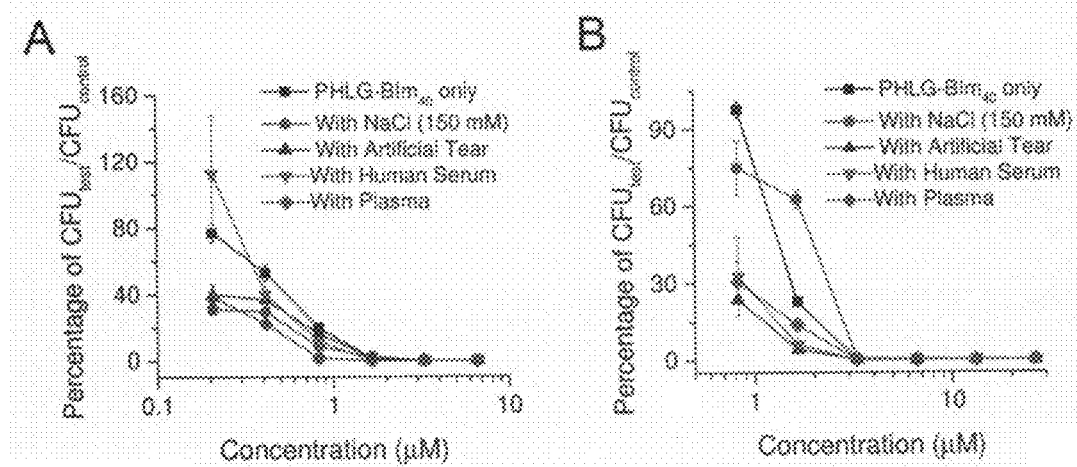
Fig. 7A-B

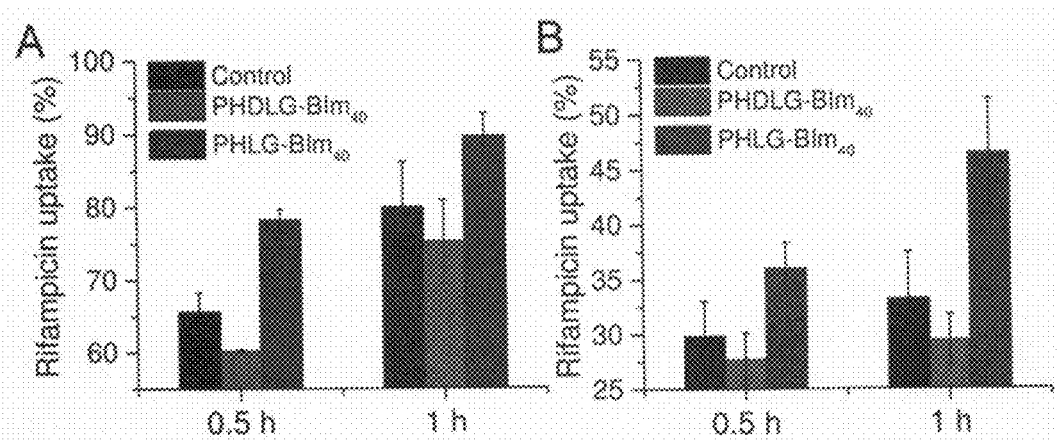
*Fig. 8A-B*
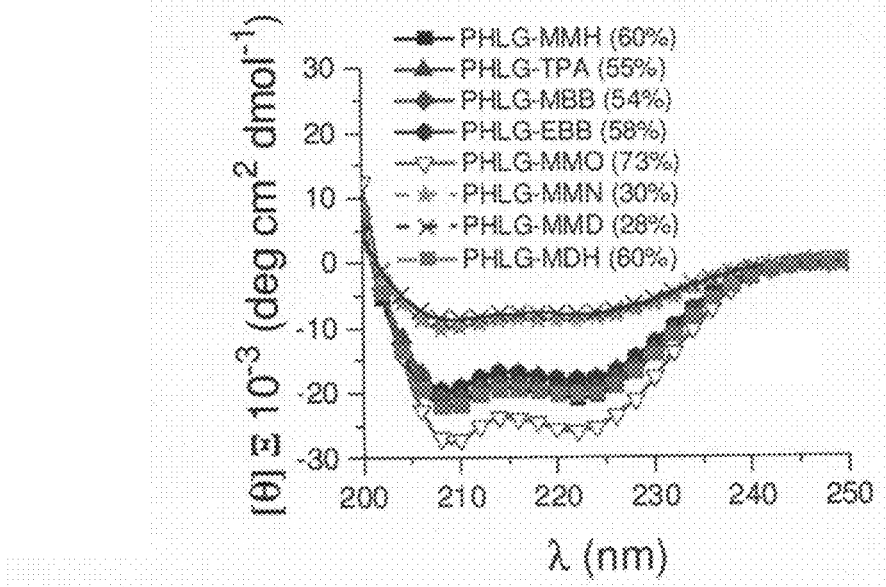
*Fig. 9*

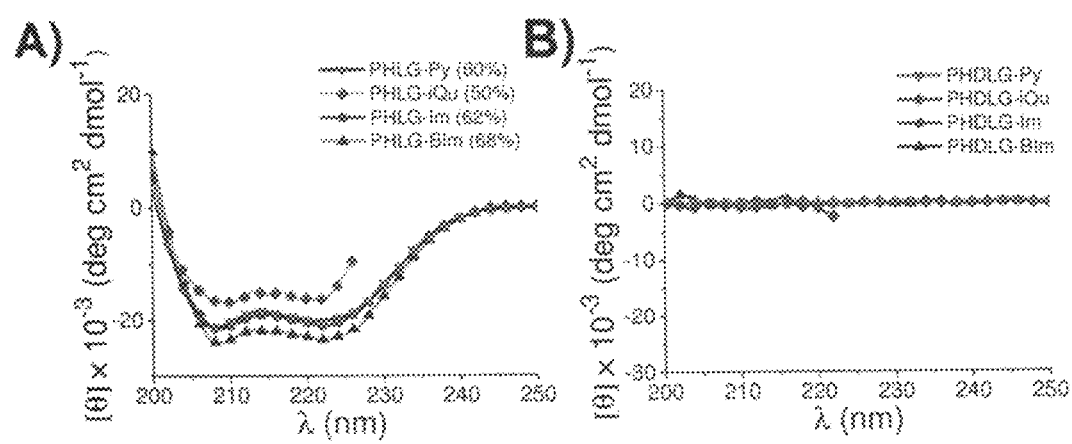
Fig. 10A-B

ANTIMICROBIAL ALPHA-HELICAL CATIONIC POLYPEPTIDES

RELATED APPLICATIONS

This application is a National Stage filing under 35 U.S.C. § 371 of International Application No. PCT/US2016/039657 filed Jun. 27, 2016, which claims priority under 35 U.S.C. § 119(e) to U.S. Provisional Patent Application No. 62/185,345, filed Jun. 26, 2015, which applications are incorporated herein by reference.

GOVERNMENT SUPPORT

This invention was made with government support under Grant No. CHE-1153122 awarded by the National Science Foundation and Award Nos. 1DP2OD007246 and 1R21EB013379, awarded by the National Institutes of Health. The government has certain rights in the invention.

BACKGROUND OF THE INVENTION

Antimicrobial peptides (AMPs) typically contain ~40-60 amino acids, consisting of both cationic and hydrophobic amino acids. They adopt various secondary structures (e.g., α-helix) and can kill a range of bacteria. As AMPs target generic and necessary lipid components of bacterial membranes and depend less on specific bacterial metabolic status, development of resistance has been slow. Because of this feature, AMPs have attracted significant attention as potential antimicrobial agents clinically. Among all AMPs developed, the α-helical peptides are the most heavily investigated, showing 'facially amphiphilic' (FA) structure with the cationic and hydrophobic amino acids separated to opposite faces of the helix. This structure correlates well to antimicrobial activity (Brogden (2005) *Nat Rev Microbiol* 3(3):238-250). Recent work has shown how amino acid content of AMPs enables this activity via specific types of membrane curvature generation (Schmidt et al. (2011) *J Am Chem Soc* 133(17):6720-6727).

Despite extensive effort, the commercial development of AMPs has seen limited success, in part due to drawbacks native to peptides. Although much has been learned from fundamental studies on AMP mechanisms, precise, quantitative predictions of an AMP's activity, therapeutic index, and antimicrobial activity compared to off-target eukaryotic cytotoxicity are currently impossible. Designing new AMP-related antibiotics relies on sequence-controlled peptide synthesis and parameter optimization, which is expensive and labor-intensive. Another drawback of most AMP-derived antibiotics is their poor stability in biological systems. LL-37 and magainin, for example, can be degraded by proteases in several minutes in blood circulation and lose their antimicrobial activities. Finally, an important drawback of AMPs is related to their 'FA' structure with hydrophobic helix face exposed (FIG. 1a), which leads to undesired polypeptide interactions with blood protein and self-aggregation. AMP helix bundles have been reported to cause substantially reduced antimicrobial activity (Bahar and Ren (2013) *Pharmaceuticals* (Basel) 6(12):1543-1575).

There has been significant interest in developing AMP analogues, such as β-peptides, α/β-peptides, peptoids, and aromatic oligomers. Some of these compounds have demonstrated improved stability over conventional AMPs. They are in general sequence-specific, and often require solid-phase peptide synthesis, thereby sharing similar advantages and development drawbacks as AMPs. There has also been growing interest in synthetic polymer-based AMP mimics bearing both cationic and hydrophobic groups, which can be prepared through cost-effective polymerization processes. For example, simplified polymeric AMP analogues have been developed, including poly(methacrylamides), poly(β-lactams), polypeptides, poly(norborenes) and poly(carbonates). These compounds are considerably less expensive than peptides, and much work is being done to optimize them.

Although some progress has been made, there is still a need for a new AMPs that can be prepared with structural and compositional control, improved in vivo stability, and that have reduced or eliminated toxicity to mammals. There is also a need for highly selective antibiotics, antibiotics that circumvent the development of resistance, and antibiotics that synergize with currently available antibiotics.

SUMMARY

A series of cationic polypeptides with stable α-helical structures bearing quaternary ammonium groups and long, hydrophobic side chains is described herein. The helical polypeptides display radial amphiphilicity and show significantly higher antibacterial activity compared to corresponding non-helical polypeptides, with high selectivity toward bacteria over mammalian cells. The helical cationic polypeptides disrupt bacteria membranes via a membrane lytic mechanism, which allows substantial circumvention of drug resistance. The membrane disruption mechanism of the helical polypeptides also increases the permeability of bacteria toward small molecule antibiotics and thus enhances and synergizes the antibacterial activity of a wide variety of commercial antibiotics. The antimicrobial helical polypeptides are therefore promising antimicrobial drugs for the treatment of various bacterial infections and related diseases.

Accordingly, the invention provides a radially amphiphilic polymer comprising Formula I:

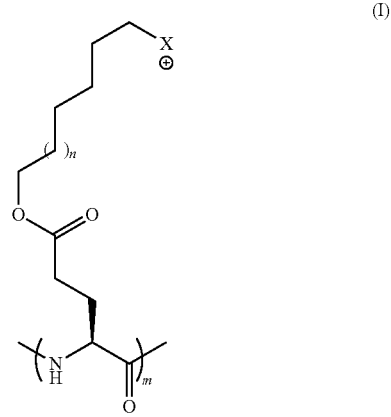

(I)

wherein m is about 6 to about 100; n is 1, 2, or 3; and X is an aliphatic, or aromatic, quaternary ammonium moiety; or a salt thereof. In one specific embodiment, the polymer comprises a polymer of Formula II:

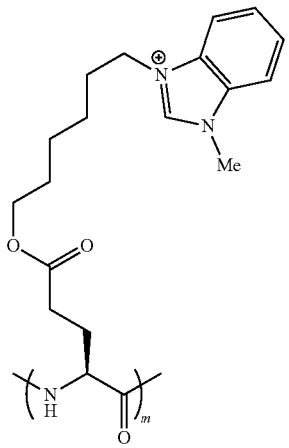
(II)

wherein m is about 6 to about 100; or a salt thereof. In various embodiments, the polymer can be a polymer of Formula III:

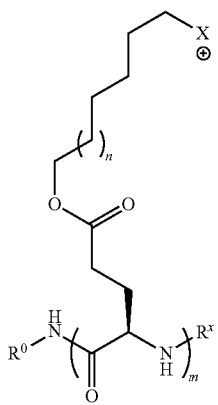
(III)

wherein $R^0$ is $(C_1$-$C_{60})$alkyl and $R^x$ is H or a silyl group; or a salt thereof.

The radially amphiphilic polymers can be used to prepare pharmaceutical compositions comprising the polymer and a pharmaceutically acceptable diluent or carrier. The pharmaceutical composition can also include a second antibiotic such as an aminoglycoside, a tetracycline, or a beta-lactam.

The invention also provides a method for inhibiting bacterial growth, or for killing bacteria, comprising contacting bacteria with a composition comprising a radially amphiphilic polymer described herein, under conditions sufficient to kill or inhibit the growth of the bacteria.

The invention further provides a method of treating a bacterial infection in a mammal comprising administering to a mammal infected with a pathogenic bacterium an effective amount of a radially amphiphilic polymer described herein, thereby treating the bacterial infection by killing the bacteria, inhibiting the growth of the bacteria, or a combination thereof. The method can include administering the radially amphiphilic polymer in combination with a second antibiotic, concurrently or sequentially. The effect of the combined administration was found to be significantly more effective than without administration of the radially amphiphilic polymer, and synergy was observed.

The invention thus provides novel peptides as described herein, intermediates for the synthesis of the peptides, as well as methods of preparing the peptides. The invention also provides novel peptides that are useful as intermediates for the synthesis of other useful compounds and compositions. The invention provides for the use of novel peptides as described herein for the manufacture of medicaments for treating bacterial infections in a mammal, such as a human. The invention therefore provides the compositions described herein for use in medical therapy. The medicament or composition can include a pharmaceutically acceptable diluent, excipient, or carrier.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

FIG. 4A-B. PHLG-BIm$_{40}$ enhances the antibacterial activity of commercial antibiotics. Antimicrobial activity of streptomycin co-delivered with PHLG-BIm$_{40}$ or PHDLG-BIm$_{40}$ at various concentrations against MG1655 ((a), MIC of PHLG-BIm$_{40}$: 26.1 µM) and C101 ((b), MIC of PHLG-BIm$_{40}$: 52.3 µM).

FIG. 5. The probability distribution of side chain lengths measured from the $C_\alpha$ to the $N_{12}$ atom extracted from the molecular simulation trajectory and averaged over all 20 side chains with a bin resolution of 0.005 nm$^{-1}$. The mode of the distribution is 1.24 nm, and the mean value is 1.15 nm with a 95% confidence interval of [0.90, 1.33] nm.

FIG. 6A-D. The killing kinetics of PHLG-BIm against DH5a (a), MG1655 (b), ATCC12608 (c) and ATCC11778 (d). PHLG-BIm was incubated with bacteria, and the colony forming units (CFU) were counted at the predetermined incubation time.

FIG. 7A-B. Percentage of (a) CFU of DH5a and (b) ATCC12608 in the samples treated with PHLG-BIm40 only, PHLG-BIm40 with NaCl (150 mM), artificial tear (2%), human serum (2%), or plasma (2%), at various concentrations for 8 h as compared to the control sample without any treatment.

FIG. 8A-B. The intracellular uptake of rifampicin in (a) MG1655 and (h) C101 after incubated with PHDLG-BIm$_{40}$ (3.3 µM) or PHLG-BIm$_{40}$ (3.3 µM) for 0.5 h and 1 h.

FIG. 9. The effect of aliphatic R group of polypeptides on the antibacterial activity and helicity. Full CD spectra of poly(L-glutamate) and poly(DL-glutamate) based polypeptides in aqueous solution at pH=7.

FIG. 10A-B. The effect of aromatic R group of polypeptides on the antibacterial activity and hemolytic activity. Full CD spectra of (a) poly(L-glutamate) and (b) poly(DL-glutamate) based polypeptides in aqueous solution at pH=7.

DETAILED DESCRIPTION

Figure 1A:
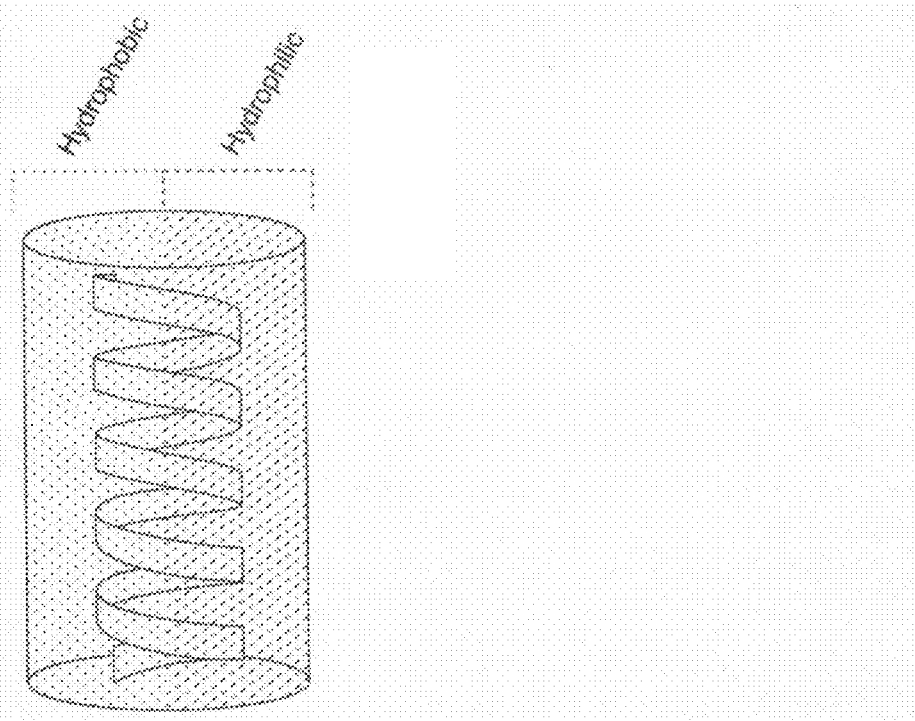
FIG. 1A-I. Schematic illustration of (a) facially amphiphilic AMP and (b) radially amphiphilic (RA) AMP. (c) The chemical structure of PHLG-BIm, where m can be about 6 to about 100. (d) CD spectra of PHLG-BIm$_{40}$ (triangle symbols), PHDLG-BIm$_{40}$ (square symbols) and PHLG-BIm$_{28}$ (circle symbols) in aqueous solution at pH=7. (e) RA peptide structure predicted from all-atom molecular dynamics simulations. Representative peptide snapshot from our simulation trajectory rendered using VMD. For clarity of viewing, the water molecules have been removed and the backbone and side chains colored in red (central core atoms) and grey (outer appendages), respectively. (f) The 3D probability distribution of the side chain N12 atoms around the α-helical backbone. (g) A 2D projection of the 3D probability distribution in FIG. 1(f) onto a plane perpendicular to the long axis of the peptide. The probability density lies in the range 0-0.83 nm$^{-2}$ and 20 evenly spaced contours plotted. (h) The stability of polypeptide PHLG-BIm$_{40}$ when incubated with trypsin, pronase, elastase from *Pseudomonas aeruginosa*, or elastase from human leukocytes for 8 h. (i) Stability of LL-37 (control peak at 4.5 min) when incubated with trypsin, pronase, elastase from *P. aeruginosa*, or elastase from human leukocytes for 8 h.

The widespread use of antibiotics is causing drug resistant bacteria to spread rapidly. Because of the widespread use, drug resistant bacteria are becoming a significant challenge in infectious disease treatments. Accordingly, there is an urgent need for new therapeutic agents due to the rapid emergence of drug resistant bacterial infections. Antimicrobial peptides (AMPs) in general have amphiphilic structure, containing both cationic amino acids and hydrophobic amino acids in a certain sequence. The amphiphilic α-helix of AMP correlates to their membrane activity and serves as a membrane-destabilizing agent, allowing the insertion of hydrophobic components into membrane lipid domains to disrupt membrane structure when the AMPs interact with bacterial membrane. The membrane physical disruption mechanism of AMP reduces the likelihood of pathogens developing resistant. However, the AMPs require a particular design to be active against the bacterial cell membrane. We describe herein a series of α-helical polypeptides bearing quaternary ammonium groups and long, hydrophobic side chains, and demonstrated that these radially amphiphilic helical polypeptides exhibit high antibacterial activity with high selectivity. Initiating the ring-opening polymerization with a large aliphatic alkylamine further enhances the antimicrobial activity of the polymers. Additionally, administration of the polymers in combination with other antibiotics enhances the activity of the second antibiotic, typically by 1-2 orders of magnitude.

Definitions

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14$^{th}$ Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrases "one or more" and "at least one" are readily understood by one of skill in the art, particularly when read in context of its usage. For example, the phrase can mean one, two, three, four, five, six, ten, 100, or any upper limit approximately 10, 100, or 1000 times higher than a recited lower limit. For example, one or more substituents on a phenyl ring refers to one to five, or one to four, for example if the phenyl ring is disubstituted.

The term "about" can refer to a variation of ±5%, ±10%, ±20%, or ±25% of the value specified. For example, "about 50" percent can in some embodiments carry a variation from 45 to 55 percent. For integer ranges, the term "about" can include one or two integers greater than and/or less than a recited integer at each end of the range. Unless indicated otherwise herein, the term "about" is intended to include values, e.g., weight percentages, proximate to the recited range that are equivalent in terms of the functionality of the individual ingredient, the composition, or the embodiment. The term about can also modify the end-points of a recited range as discuss above in this paragraph.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "alkyl" refers to a branched or unbranched hydrocarbon having, for example, from 1-20 carbon atoms or about 5 to about 15 carbons, and often 1-12, 1-10, 1-8, 1-6, or 1-4 carbon atoms. Examples include, but are not limited to, methyl, ethyl, 1-propyl, 2-propyl (iso-propyl), 1-butyl, 2-methyl-1-propyl (isobutyl), 2-butyl (sec-butyl), 2-methyl-2-propyl (t-butyl), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, hexyl, octyl, decyl, dodecyl, and the like. The alkyl can be unsubstituted or substituted, for example, with a substituent described below. The alkyl can be a branched alkyl, such as saturated isoprene groups of 5, 10, or 15 carbon atoms. The alkyl can be a monovalent hydrocarbon radical, as described and exemplified above, or it can be a divalent hydrocarbon radical (i.e., an alkylene).

The term "heteroaryl" refers to a monocyclic, bicyclic, or tricyclic ring system containing one, two, or three aromatic rings and containing at least one nitrogen, oxygen, or sulfur atom in an aromatic ring. When the heteroaryl contains a nitrogen, it can be X of Formula I or III. The heteroaryl can be unsubstituted or substituted, for example, with one or more, and in particular one to three, substituents, as described in the definition of "substituted". Typical heteroaryl groups contain 2-20 carbon atoms or 5-9 carbon atoms in the ring skeleton in addition to the one or more heteroatoms. Examples of heteroaryl groups include, but are not limited to, 2H-pyrrolyl, 3H-indolyl, 4H-quinolizinyl, acridinyl, benzo[b]thienyl, benzothiazolyl, β-carbolinyl, carbazolyl, chromenyl, cinnolinyl, dibenzo[b,d]furanyl, furazanyl, furyl, imidazolyl, imidizolyl, indazolyl, indolisinyl, indolyl, isobenzofuranyl, isoindolyl, isoquinolyl, isothiazolyl, isoxazolyl, naphthyridinyl, oxazolyl, perimidinyl, phenanthridinyl, phenanthrolinyl, phenarsazinyl, phenazinyl, phenothiazinyl, phenoxathiinyl, phenoxazinyl, phthalazinyl, pteridinyl, purinyl, pyranyl, pyrazinyl, pyrazolyl, pyridazinyl, pyridyl, pyrimidinyl, pyrrolyl, quinazolinyl, quinolyl, quinoxalinyl, thiadiazolyl, thianthrenyl, thiazolyl, thienyl, triazolyl, tetrazolyl, and xanthenyl, and dimers thereof. In one embodiment the term "heteroaryl" denotes a monocyclic aromatic ring containing five or six ring atoms containing carbon and 1, 2, 3, or 4 heteroatoms independently selected from non-peroxide oxygen, sulfur, and N(Z) wherein Z is absent or is H, O, alkyl, aryl, or aryl($C_1$-$C_6$) alkyl- (e.g., benzyl). In some embodiments, heteroaryl denotes an ortho-fused bicyclic heterocycle of about eight to ten ring atoms derived therefrom, particularly a benz-derivative or one derived by fusing a propylene, trimethylene, or tetramethylene diradical thereto.

By way of example and not limitation, nitrogen bonded heterocycles can be bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. In one embodiment, nitrogen bonded heterocycles include 1-aziridyl, 1-azetedyl, 1-pyrrolyl, 1-imidazolyl, 1-pyrazolyl, and 1-piperidinyl. The heterocycles are covalently bonded to the polypeptide backbone of the polypeptides described herein via the hydrophobic side chain, wherein there are typically 11-13 sigma bonds between the polypeptide backbone and the quaternary nitrogen of the heterocycle (quaternary as a result of the bonding to the polymer side chain), which results in a charged nitrogen in the heterocyclic ring.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

An "effective amount" refers to an amount effective to treat a disease, disorder, and/or condition, or to bring about a recited effect. For example, an effective amount can be an amount effective to reduce the progression or severity of the condition or symptoms being treated. Determination of a therapeutically effective amount is well within the capacity of persons skilled in the art. The term "effective amount" is intended to include an amount of a compound described herein, or an amount of a combination of compounds described herein, e.g., that is effective to treat or prevent a disease or disorder, or to treat the symptoms of the disease or disorder, in a host. Thus, an "effective amount" generally means an amount that provides the desired effect.

The terms "treating", "treat" and "treatment" include (i) inhibiting the disease, pathologic or medical condition or arresting its development; (ii) relieving the disease, pathologic or medical condition; and/or (iii) diminishing symptoms associated with the disease, pathologic or medical condition. Thus, the terms "treat", "treatment", and "treating" can include lowering, lessening, stopping or reversing the progression or severity of the condition or symptoms being treated. As such, the term "treatment" can include medical and therapeutic administration, as appropriate.

Treatments may be reactive, such as for combating an existing infection, or prophylactic, for preventing infection in an organism susceptible to infection. In some embodiments, compositions can be used to treat infections by drug-resistant strains of bacteria, for example MRSA (methicillin resistant *S. aureus*), MRSE (methicillin resistant *S. epidermidis*), PRSP (penicillin resistant *S. pneumoniae*), VIRSA (vancomycin intermittently resistant *Staphylococcus aureus*) or VRE (vancomycin resistant Enterococci). The term "drug-resistant" is a condition where the bacteria are resistant to treatment with one or more conventional antibiotics, particularly β-lactam antibiotics. Accordingly, the invention provides a method for killing or inhibiting growth of Gram-positive bacteria comprising contacting Gram-positive bacteria with a polymer described herein, thereby killing or inhibiting the growth of the bacteria. The contacting can be performed in vivo in a human or animal, or in vitro, for example, in an assay. The Gram-positive bacteria can be of the genus *Enterococcus* or *Staphylococcus*. In certain embodiments, the bacteria is a drug-resistant strain of the genus *Staphylococcus*. In certain specific embodiments, the bacteria is a methicillin-resistant *Staphylococcus aureus* (MRSA) strain.

In some embodiments, the bacterial infection may be due to Gram-positive bacteria, including, but not limited to, methicillin resistant *Staphylococcus aureus* (MRSA), community-acquired methicillin resistant *Staphylococcus aureus* (CAMRSA), vancomycin-intermediate-susceptible *Staphylococcus aureus* (VISA), methicillin-resistant coagulase-negative staphylococci (MR-CoNS), vancomycin-intermediate-susceptible coagulase-negative staphylococci (VI-CoNS), methicillin susceptible *Staphylococcus aureus* (MSSA), *Streptococcus pneumoniae* (including penicillin-resistant strains [PRSP]) and multi-drug resistant strains [MDRSP]), *Streptococcus agalactiae*, *Streptococcus pyogenes* and *Enterococcus faecalis*. In particular embodiments, the bacterial infection may include, but is not limited to, complicated skin and skin structure infections (cSSSI); community acquired pneumonia (CAP); complicated intra-abdominal infections, such as, complicated appendicitis, peritonitis, complicated cholecystitis and complicated diverticulitis; uncomplicated and complicated urinary tract infections, such as, pyelonephritis; and respiratory and other nosocomial infections.

The term "infection" refers to the invasion of the host by germs (e.g., bacteria) that reproduce and multiply, causing disease by local cell injury, release of poisons, or germ-antibody reaction in the cells. The compounds and compositions described herein can be used to treat a Gram-positive or Gram-negative bacterial infection, for example, an infection in a mammal, such as a human.

The terms "inhibit", "inhibiting", and "inhibition" refer to the slowing, halting, or reversing the growth or progression of a disease, infection, condition, or group of cells. The inhibition can be greater than about 20%, 40%, 60%, 80%, 90%, 95%, or 99%, for example, compared to the growth or progression that occurs in the absence of the treatment or contacting.

Bacteria are prokaryotic microorganisms. The AMPs described herein can inhibit and kill pathogenic bacteria, such as when a mammal is infected with the bacteria and the AMPs are administered to the mammal. Accordingly, the AMPs described here can be used to treat infections caused by bacteria of a variety of genera, including *Acinetobacter, Actinobacillus, Anaplasma, Bacillus, Bacteroides, Bifidobacterium, Bordetella, Brucella, Burkholderia, Campylobacter, Chlamydia, Clostridium, Corynebacterium, Ehrlichia, Escherichia, Francisella, Fusobacterium, Haemophilus, Helicobacter, Leptospira, Listeria, Mannheimia, Moraxella, Mycobacterium, Mycoplasma, Neisseria, Neorickettsia, Pasteurella, Porphyromonas, Prevotella, Pseudomonas, Psychrobacter, Salmonella, Serratia, Shewanella, Shigella, Tannerella, Treponema, Tropheryma, Vibrio, Wolbachia, Yersinia, Plasmodium*, and *Toxoplasma*, as well as *Eubacterium, Gardnerella, Klebsiella, Peptostreptococcus, Proteus, Providencia*, and *Cryptosporidium* in various embodiments.

Specific examples of species of such genera include, for example, *Acinetobacter* sp., *Actinobacillus pleuropneumonias, Actinobacillus actinomycetemcomitans, Anaplasma phagocytophilum, Bacillus anthracis, Bacillus cereus, Bacteroides fragilis, Bacteroides thetaiotaomicron, Bifidobacterium longum, Bordetella bronchiseptica, Bordetella pertussis, Brucella melitensis, Brucella suis, Burkholderia cepacia, Burkholderia mallei, Burkholderia pseudomallei, Campylobacter jejuni, Chlamydia trachomatis, Chlamydophila pneumoniae, Clostridium botulinum, Clostridium perfringens, Clostridium diffcile, Clostridium tetani, Corynebacterium diphtherias, Ehrlichia chaffeensis, Escherichia coli, Francisella tularensis, Fusobacterium nucleatum, Haemophilus ducreyi, Haemophilus influenzae, Helicobacter pylori, Leptospira interrogans, Listeria monocytogenes, Mannheimia haemolytica, Moraxella catarrhalis, Mycobacterium leprae, Mycobacterium smegmatis, Mycobacterium tuberculosis, Mycoplasma penetrans, Neisseria gonorrhoeae, Neisseria meningitides, Neorickettsia sennetsu, Pasteurella multocida, Porphyromonas gingivalis, Prevotella intermedia, Pseudomonas aeruginosa, Pseudomonas putida, Psychrobacter* sp., *Salmonella enterica, Salmonella enteritidis, Salmonella typhimurium, Serratia marcescens, Shewanella putrefaciens, Shigella flexneri, Shigella dysenteriae, Tannerella forsythensis, Treponema denticola, Treponema pallidum, Tropheryma whipplei, Vibrio cholerae, Vibrio vulnificus, Wolbachia* sp., *Yersinia pestis, Yersinia enterocolitica, Plasmodium falciparum, Plasmodium vivax*, and *Toxoplasma gondii*, as well as in some embodiments, *Eubacterium* sp., *Gardnerella vaginalis, Klebsiella pneumoniae, Peptostreptococcus* sp., *Proteus mirabilis, Providencia stuartii*, and *Cryptosporidium parvum*. The AMPs described herein can be used to treat infections caused by any one or more of the above genera or species, or the AMPs can be used to kill or inhibit the growth of such bacteria, for example, in vivo, or in vitro, such as in a patient, in a solution, or in or on a grown medium.

Various Embodiments of Antimicrobial Polypeptides with Radial Amphiphilicity

As described above, the invention provides a radially amphiphilic polymer comprising Formula I:

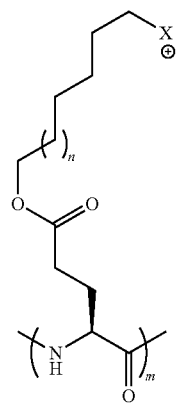
(I)

wherein m is about 6 to about 100; n is 1, 2, or 3; and X is an aliphatic or aromatic quaternary ammonium moiety; or a salt thereof. In typical embodiments, the polymer is in the form of an α-helix.

In some embodiments, m is about 10 to about 80, or about 25 to about 50. The value of n can be 1, for example, when CH-L-Glu is prepared using a hexyl halide. The value of n can be 2 or 3 when the monomer is prepared using a heptyl halide or octyl halide.

In some embodiments, X is an aromatic quaternary ammonium moiety comprising 3 to 13 carbon atoms, 5 to 13 carbon atoms, or 8 to 13 carbon atoms. The aromatic quaternary ammonium moiety can be, for example, a pyridyl, quinolinyl, imidazolyl, or benzimidazolyl group that is covalently bound to the side chain of the polymer at a nitrogen of the nitrogen heterocycle. The aromatic group can be unsubstituted or substituted, for example, with $(C_1-C_{10})$alkyl groups or other substituents of nitrogen-containing aromatic groups. In certain specific embodiments, X can be:

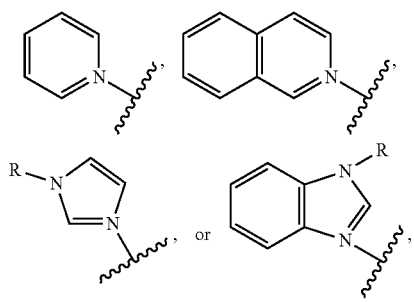

wherein R is $(C_1-C_{10})$alkyl.

In other embodiments, X is an aliphatic quaternary ammonium moiety comprising about 3 to about 13 carbon atoms, or about 8 to about 13 carbon atoms. In some embodiments, X is:

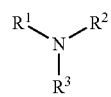

wherein $R^1$, $R^2$, and $R^3$ are each straight chain or branched $(C_1-C_{10})$alkyl, wherein the total number of carbon atoms in $R^1$, $R^2$, and $R^3$ combined is 3 to about 36, or 3 to 13. In certain specific embodiments, X is:

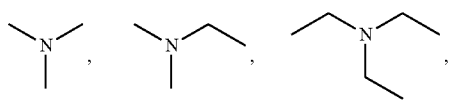

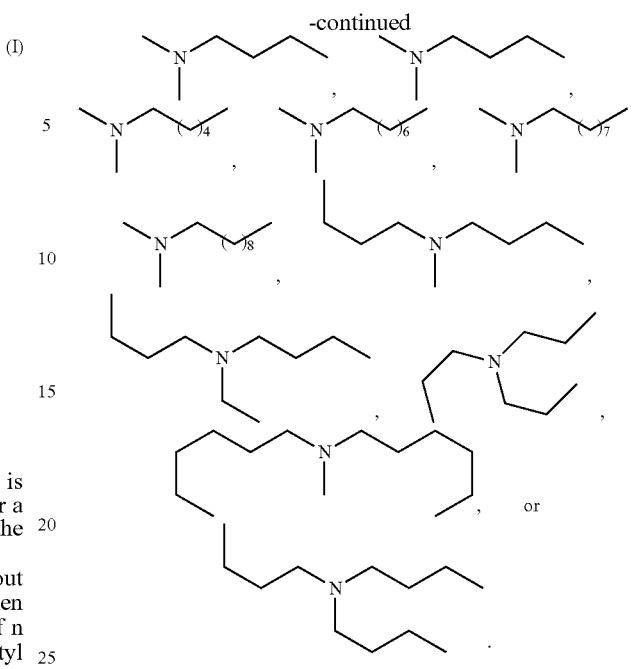

In one specific embodiment, the polymer comprises Formula II:

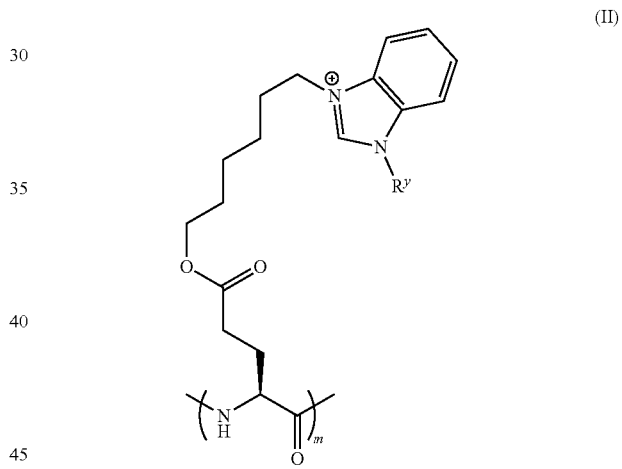

(II)

wherein m is about 6 to about 100, and $R^y$ is $(C_1-C_{10})$alkyl, for example, methyl; or a salt thereof. In other specific embodiments, the polymer is a polymer of Formula III:

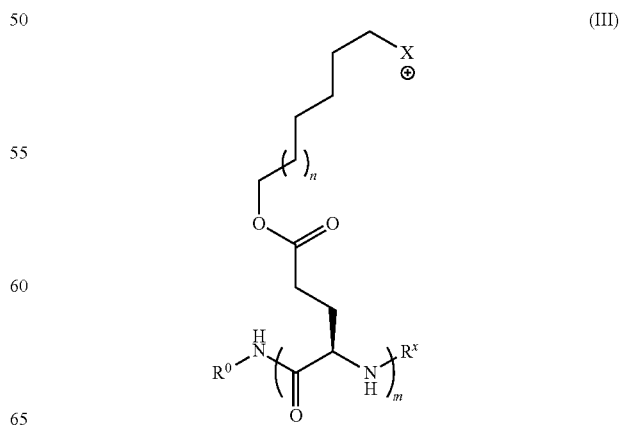

(III)

wherein $R^o$ is $(C_1-C_{60})$alkyl and $R^x$ is H or a silyl group (depending on how the ring-opening polymerization to prepare the polymer is quenched). The silyl group can be, for example, TMS. In various embodiments, $R^0$ is a straight chain or branched $(C_1-C_{60})$alkyl. Examples of $R^0$ include

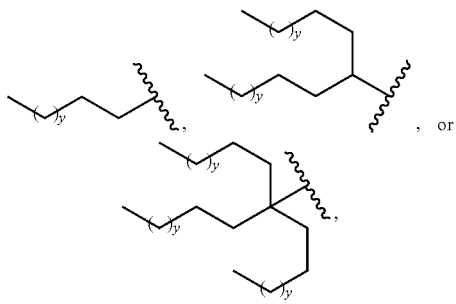

where each y is independently 0 to about 16.

The invention also provides a pharmaceutical composition comprising a radially amphiphilic polymer described herein and a pharmaceutically acceptable diluent or carrier, and/or a second antibiotic. The second antibiotic can be, for example, an aminoglycoside, a tetracycline, or a beta-lactam. Specific examples of the second antibiotic include streptomycin, gentamicin, doxycycline, rifampicin, and penicillin, as well as the antibiotics recited herein.

The polymers and their compositions can be used in a method for inhibiting bacterial growth, or for killing bacteria, the method comprising contacting bacteria with a composition comprising a radially amphiphilic polymer described herein, under conditions sufficient to kill or inhibit the growth of the bacteria.

The invention thus further provides a method of treating a bacterial infection in a mammal comprising administering to a mammal infected with a pathogenic bacterium an effective amount of a polymer described herein, thereby treating the bacterial infection by killing the bacteria, inhibiting the growth of the bacteria, or a combination thereof.

The bacteria can be Gram-positive bacteria, or they can be Gram-negative bacteria.

The method can include contacting the bacteria with a second antibiotic, concurrently or sequentially. The activity of the combination of the polymer and the second antibiotic can have synergistic activity toward the bacterial infection. The presence of the radially amphiphilic polymer can enhance antimicrobial activity of the second antibiotic by 1-2 orders of magnitude.

In other embodiments, the same activity can be achieved by administering about 0.1 to about 0.01 times the amount of the second antibiotic otherwise needed to achieve effective antibacterial activity.

Helical Antimicrobial Polypeptides with Radial Amphiphilicity

α-Helical antimicrobial peptides (AMPs) generally have facially amphiphilic structures. The facial amphiphilicity leads to undesired peptide interactions with blood protein and self-aggregation due to the exposed hydrophobic surface. This disclosure describes the design of a class of cationic, helical homo-polypeptide antimicrobials with a hydrophobic internal helical core and a charged exterior shell, possessing unprecedented radial amphiphilicity.

The radially amphiphilic structure enables the polypeptide to bind effectively to the negatively charged bacterial surface, and exhibit high antimicrobial activity against both Gram-positive and Gram-negative bacteria. Moreover, the shielding of the hydrophobic core by the charged exterior shell decreases non-specific interactions with eukaryotic cells, showing low hemolytic activity, and protects the polypeptide backbone from proteolytic degradation. The radially amphiphilic polypeptides can also be used as effective adjuvant, allowing improved permeation of commercial antibiotics in bacteria and enhanced antimicrobial activity by 1-2 orders of magnitude. We have thus designed AMPs bearing the unprecedented, unique radially amphiphilic structure, which represents a new, alternative direction of AMP development. The radially amphiphilic polypeptides provide a general platform for treating drug-resistant bacteria.

Described herein is a fundamentally different design of AMPs with 'radially amphiphilic' (RA) structure (FIG. 1B) rather than 'FA' structure (FIG. 1A). These new antimicrobial homo-polypeptides have a hydrophobic helical core covered with cationic groups in all radial directions of the helix. Because the charged groups are on the outer shell of the polypeptides with hydrophobic helical core shielded, these peptides have minimal hydrophobic force induced self-aggregation and reduced interaction with blood proteins. With such RA structure, the polypeptide backbone amide bonds are well-protected and have improved stability against proteolytic degradation compared to a typical α-helical AMP that does not possess radial amphiphilicity.

We have thus developed a new class of cationic, helical antimicrobial homo-polypeptides with unprecedented radial amphiphilicity. Unlike typical AMPs characterized by facial amphiphilicity or biomimetic antimicrobial polymers with randomly distributed charged and hydrophobic groups, these new AMPs are homo-polypeptides with RA structure. They adopt a stable α-helical conformation with a hydrophobic helical core and a charged exterior shell, formed by long hydrophobic side chains (e.g., having 11-13 sigma bonds between the polymer backbone and the charge, and no cyclic moieties) and the terminal charge group (e.g., aliphatic or aromatic quaternary ammonium moiety).

The RA polypeptides offer several advantages over typical AMPs. They can be easily synthesized through controllable NCA polymerization followed by side chain modification, typically with at least 70% conversion of the side chains to charged quaternary nitrogen groups, often greater than 90% or 95%. The RA structure enables the polypeptides to bind effectively to the negatively charged bacterial surface, and exhibit high antimicrobial activity against both Gram-positive and Gram-negative bacteria. Moreover, the shielding of the hydrophobic core by the charged exterior shell decreases non-specific interactions with eukaryotic cells and contributes to low mammalian cytotoxicity.

The polypeptides also demonstrate excellent stability against enzymatic degradation, potentially due to suppressed protease access to the polypeptide backbone. In addition, the antibacterial and hemolytic activities of the RA polypeptides can be tuned by varying the terminal amine group and the hydrophobicity of helical core, both of which can be easily attainable based on the techniques described in our previous studies (Yin et al. (2013) *Angew Chem Int Edit* 52(22):5757-5761; Lu et al. (2011) *Nat Commun* 2:206; Gabrielson et al. (2012) *Angew Chem Int Edit* 51(5):1143-1147). Thus, the RA polypeptides provide an excellent platform for the design of new AMP analogues.

The antibacterial activity of these RA polypeptides likely results from electrostatic interactions between their cationic groups and anionic bacteria cell membranes, followed by the disruption of the bacteria cell membranes by the membrane-active polypeptide helix. Additional factors are involved in bacterial membrane destabilization, as indicated by our SAXS studies on model bacterial membranes in which helical polypeptide PHLG-BIm promoted saddle-shaped membrane deformations (negative Gaussian curvature, NGC), a topological requirement for membrane destabilizing events such as pore-formation. All tested model membranes had a fixed anionic charge, yet we observed selective generation of NGC in the PE-rich bacteria model membrane. This is consistent with previous work, which showed that membranes with greater amounts of negative intrinsic curvature lipids promote destabilization and are more susceptible to pore formation (Yang et al. (2008) *Proc Natl Acad*

Sci USA 105(52): 20595-20600). Moreover, both anionic and negative intrinsic curvature lipids are necessary for activity, while neither alone is sufficient. Therefore, the preference for the helical polypeptides to generate NGC at high PE content points to a mechanism of selectivity that involves membrane curvature effects.

The observed synergistic bactericidal effect results from increased cellular penetration of antibiotics that is facilitated by the membrane permeabilization activity of the polypeptides. Induced NGC is broadly enabling in the context of membrane permeation mechanisms, such as transmembrane pores, blebbing, budding, and scission. The permeation can involve a hierarchy of mechanisms. We observe NGC in the form of a cubic phase; the size of the defect on a 2D membrane will depend on the type of defect it is. The Pn3m cubic phase induced by the polypeptide PHLG-BIm$_{40}$ has an average Gaussian curvature (K) value of $-0.01065$ nm$^{-2}$. For example, this is the amount of NGC found in a transmembrane pore with a size of ~40 nm, if we ignore all other effects. If on the other hand, the destabilization mechanism is that of a budding event followed by scission, then we can estimate the size of the defect using a catenoid surface, which is an approximate representation of the surface of a scission pore (Boucrot et al. (2012) *Cell* 149(1):124-136; Schmidt et al. (2013) *J Am Chem Soc* 135(37):13710-13719). The Gaussian curvature of a minimal catenoid surface with a neck radius of c along its z-axis is defined by: $K(z)=-[sech^4(z/c)]/c^2$. The measured (K) value corresponds to a catenoid neck diameter of ~19.4 nm. If we account for the approximate bilayer membrane thickness of 4 nm, this diameter translates to a pore size of ~15.4 nm. In both of the above cases, the size of the defect is significantly larger than the size of a typical antibiotic. Thus, designing AMPs bearing the unique RA structure represents a new, alternative direction of AMP development. The RA-polypeptide can thus be a general platform for developing AMP formulations to treat drug-resistant bacteria.

RA Polypeptide Displays High Antibacterial Activity and Selectivity.

Figure 1B:
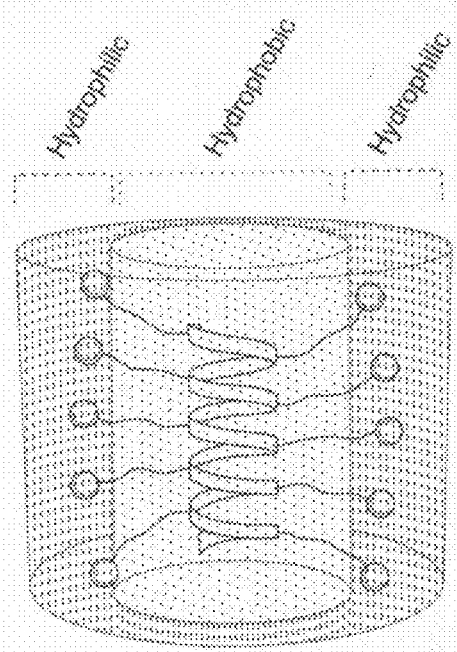
Figure 1C:
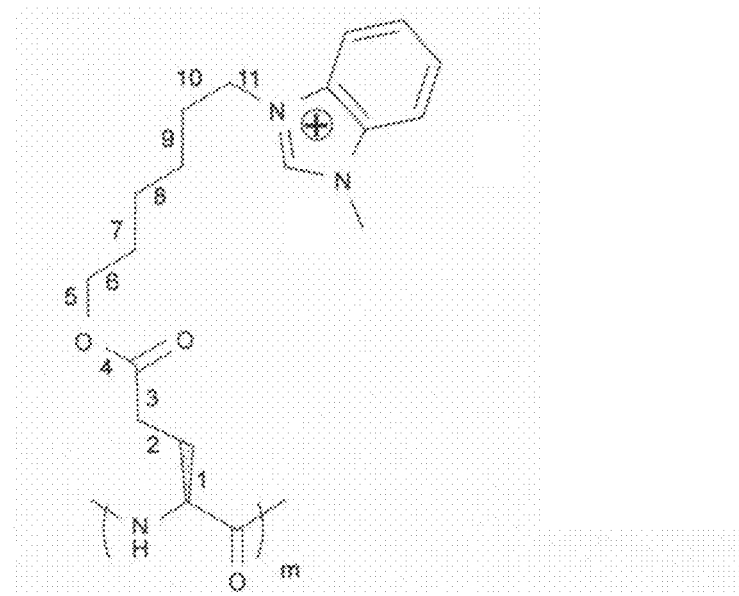

The radially amphiphilic, helical, charged polypeptides with long hydrophobic side chains and cationic terminal groups described herein demonstrated remarkable helical stability against changes in pH, salts, temperature and various denaturing conditions. The RA polypeptides were explored for applications as new AMPS. One specific cationic α-helical polypeptide with RA structure is PHLG-BIm (FIG. 1C). It was synthesized through ring-opening polymerization of amino acid N-carboxyanhydrides (NCAs) (see Lu and Cheng (2007) *J Am Chem Soc* 129(46):14114-14115), followed by amination with 1-methylbenzimidazole (Scheme 1) (see also, U.S. Pat. No. 9,243,040, which is incorporated herein by references, for useful synthetic techniques).

Scheme 1. Synthesis of antibacterial PHLG-based polypeptides

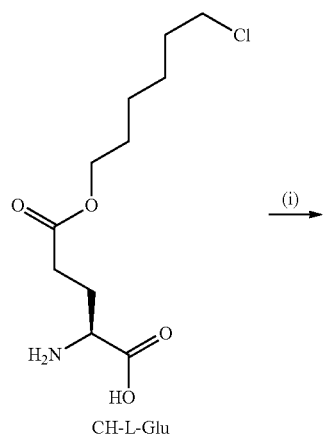

CH-L-Glu

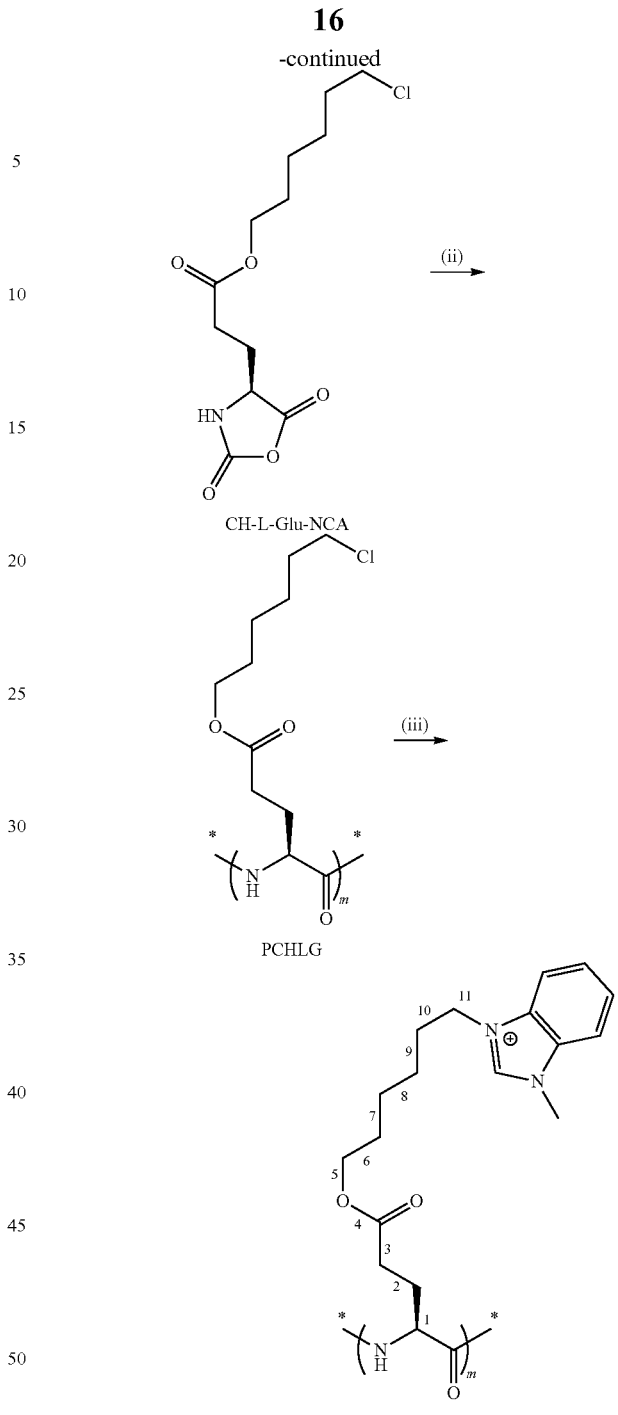

Figure 1D:
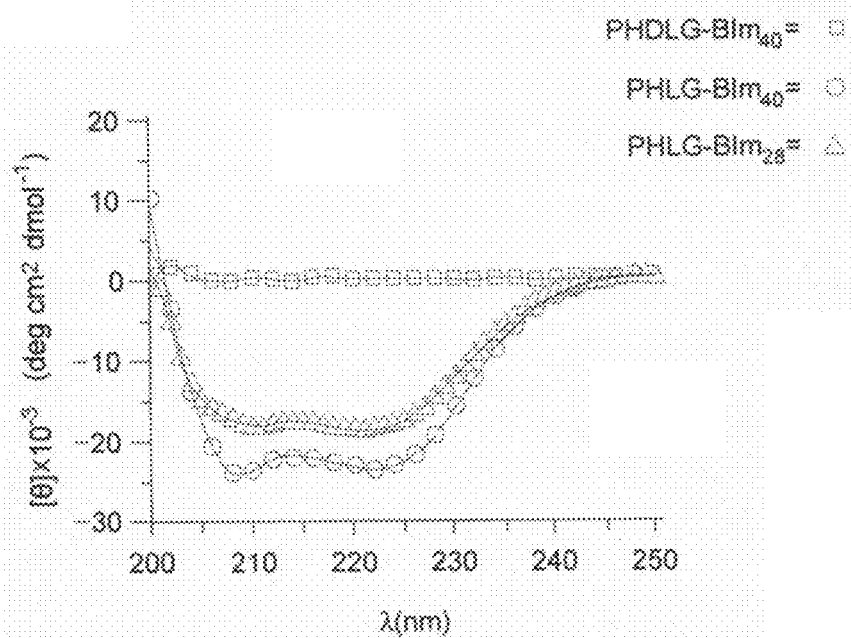

PHLG-BIm (i) phosgene; (ii) HDMS/DMF; (iii) tertiary amine (e.g., 1-methylbenzimidazole (BIm)), NaI, DMF/MeCN With a separation of 11 σ-bonds between the backbone and positive charges, PHLG-BIm, with DP anywhere from about 6 to about 100, adopts α-helical conformation. Specific examples having DP of 40 and 28 were representative and were further evaluated. The α-helical conformations were evident from the characteristic double minima at 208 and 222 nm in the Circular Dichroism (CD) spectra at a concentration of 0.40 mg/mL in water (FIG. 1D). The corresponding non-helical PHDLG-BIm$_{40}$ was synthesized through the polymerization of DL-NCA to study the effect of helical structure on the antibacterial activity of polypeptide.

Figure 1E:
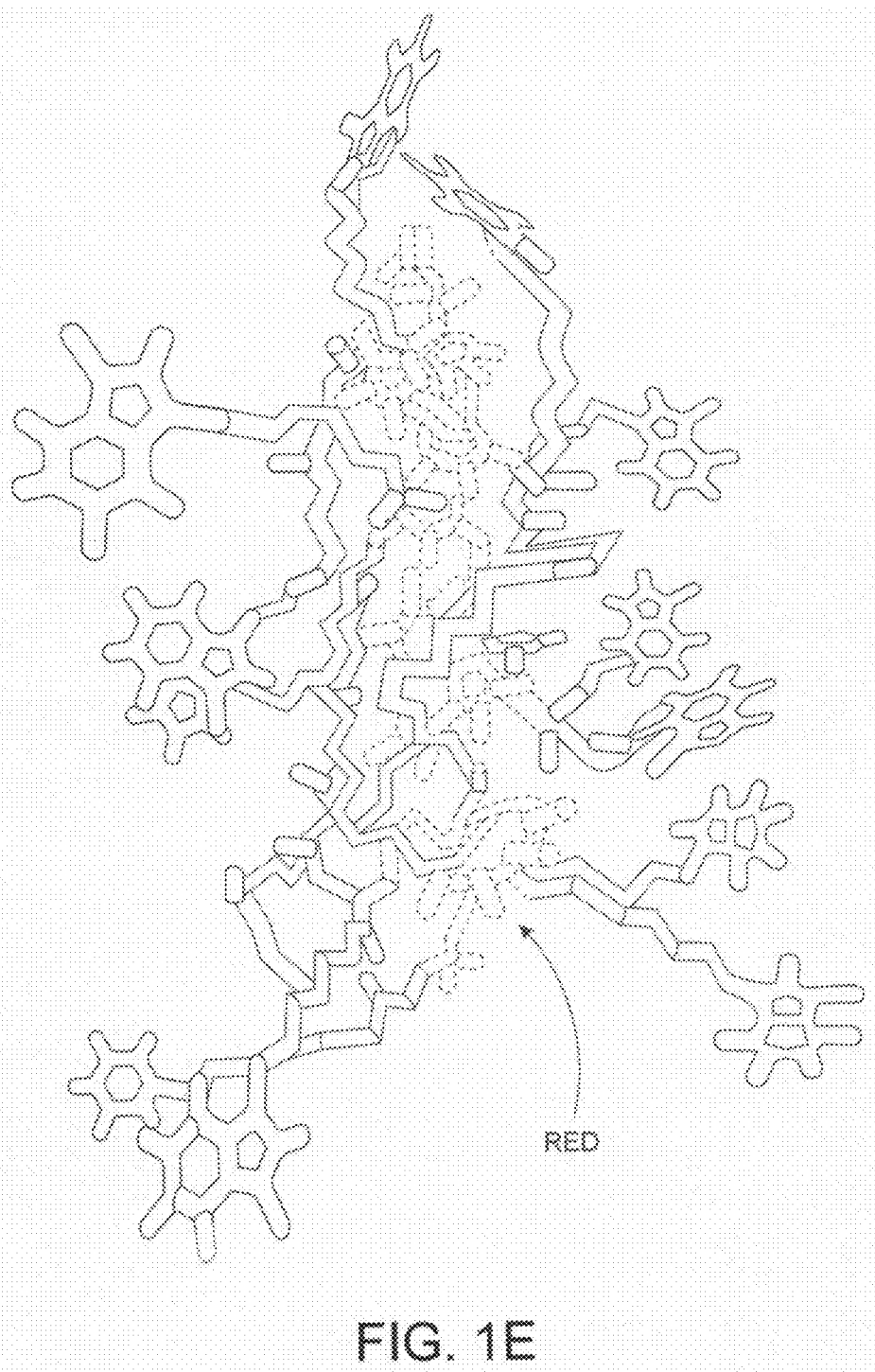

Our molecular simulations provide molecular-level theoretical support for the RA structure. A simulation snapshot in FIG. 1E illustrates the cationic side chains forming a hydrophilic shell around the hydrophobic aliphatic side chains and helical core. Discounting the two terminal residues to eliminate end effects, the peptide backbone is close to the ideal helix, $\text{RMSD}_{helix}=(0.04\pm0.01)$ nm, with a radius $r_{helix}=(0.232\pm0.002)$ nm and twist $\gamma_{helix}=(100\pm1°)$ also nearly ideal ($r_{helix}^{ideal}=0.23$ nm, $\gamma_{helix}^{ideal}=100°$). The mean per residue molar ellipticity at 222 nm computed from our simulations using Dichro-Calc (comp.chem.nottingham.ac.uk/cgi-bin/dichrocalc/bin/getparams.cgi) (Bulheller and Hirst (2009) *Bioinformatics* 25(4):539-540) of $[\theta]_{222\ nm}=(-21\pm1)\times10^{-3}$ deg·cm$^2$/dmol is in excellent agreement with the experimental value of $-23\times10^{-3}$ deg·cm$^2$/dmol for PHLG-BIm$_{40}$ and $-19\times10^{-3}$ deg·cm$^2$/dmol for PHLG-BIm$_{28}$ reported in FIG. 1D.

Figure 1F:
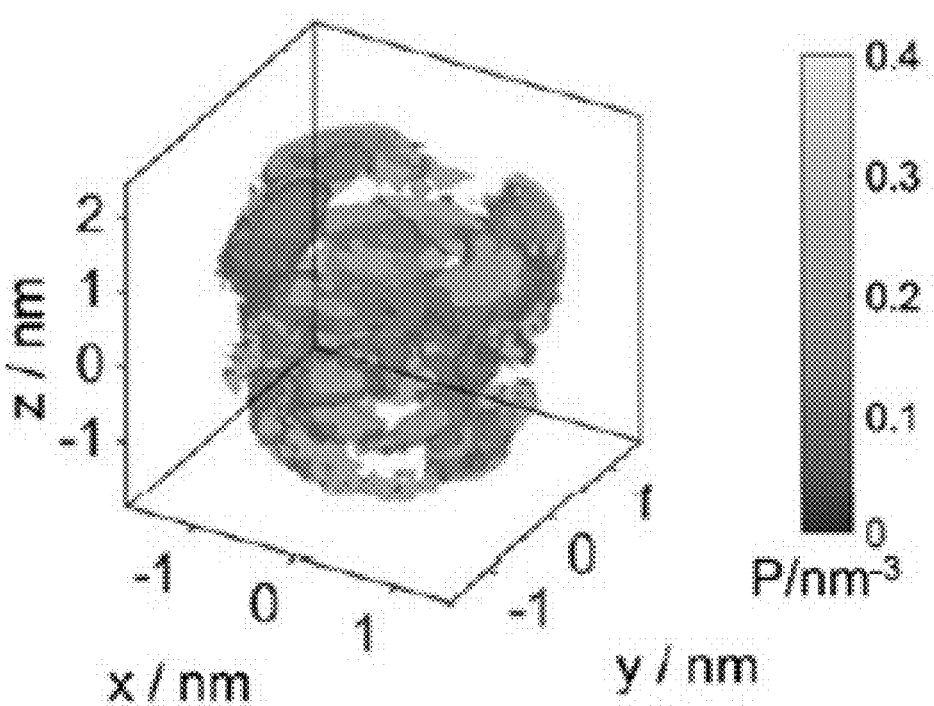
Figure 1G:
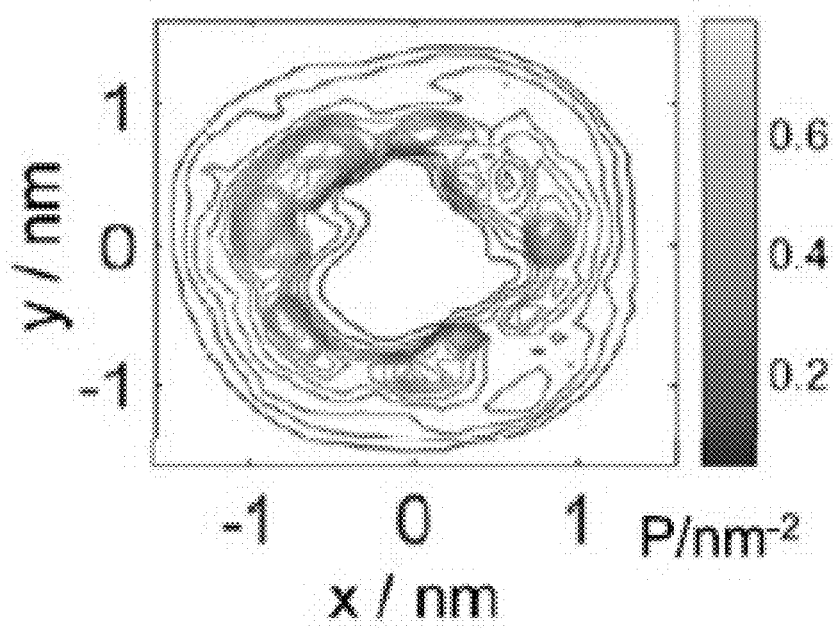

To quantify the RA structure we computed the probability distribution of the side chain N12 atoms after aligning the peptide backbone to a reference structure and discarding the four side chains at the termini to eliminate end effects (FIG. 1F, 1G) (using MATLAB 2014a). We also measured the probability distribution of side chain lengths from the Cα to the N12 atom. The mode of the distribution is 1.24 nm, and the mean value is 1.15 nm with a 95% confidence interval of [0.90, 1.33] nm (FIG. 5). The result was further confirmed by nuclear overhauser effect (NOE) spectroscopy, with no NOE detected between protons around the nitrogen atoms on the benzimidazole ($N_{12}$) (d, b, b', c, c', e) and protons around $C_\alpha$ (h, i, g). Since the positive charge in the cationic side chains resides primarily in the termini, these distributions are a proxy for the positive charge distribution, providing strong support for an RA structure.

The antibacterial activity of PHLG-BIm was evaluated by the minimal inhibitory concentration (MIC) of the polypeptide against bacteria (Andrews (2002) *J Antimicrob Chemother* 49(6):1049-1050). With RA structure, PHLG-BIm$_{40}$ showed strong antibacterial activities against both Gram-negative bacteria, DH5α, MG1655, and Gram-positive bacteria, ATCC12608, ATCC11778, with MIC values of 3.3, 26.1, 13.1 and 13.1 respectively (Table 1).

TABLE 1

The antibacterial and hemolytic activity of polypeptides. The antibacterial activity of polypeptides was determined using minimal inhibitory concentration (MIC). The hemolytic activity of polypeptides was determined by HC50 (50% hemolytic concentration) value.

| | MIC (μM) | | | | | | | | | | | | | HC50 |
|---|---|---|---|---|---|---|---|---|---|---|---|---|---|---|
| | DH5 | MG16 | ATCC | ATCC1 | | Clinical isolated *H. pylori* | | | | | | MRSA | | |
| Polypeptide | α | 55 | 12608 | 1778 | B107 | J291 | J99 | J99-AF | J99-A9 | J99-A11 | NRS382 | NRS383 | NRS384 | (μM) |
| PHLG-BIm$_{40}$ | 3.3 | 26.1 | 13.1 | 13.1 | 6.6 | 1.5 | 3.3 | 3.3 | 1.5 | 3.3 | 1.5 | 1.5 | 1.5 | >104.6 |
| PHDLG-BIm$_{40}$ | 52.3 | 104.6 | 52.3 | 52.3 | 26.1 | 6.6 | 13.1 | 26.1 | 6.6 | 26.1 | 26.1 | 6.6 | 6.6 | >104.6 |
| PHLG-BIm$_{28}$ | 9.4 | 37.3 | 18.7 | 18.7 | 18.7 | 4.3 | 9.4 | 9.4 | 4.3 | 9.4 | 2.1 | 2.1 | 2.1 | >149.4 |

The helical PHLG-BIm$_{40}$ showed higher antibacterial activity than the non-helical PHDLG-BIm$_{40}$, with MIC values 16, 4, 4 and 4 times lower against DH5a, MG1655, ATCC12608, and ATCC11778, respectively. Length was also found to influence the antimicrobial activity of the RA polypeptides, as PHLG-BIm$_{28}$, with DP of 28, showed slightly lower antimicrobial activity compared with PHLG-BIm$_{40}$. We also tested the antimicrobial activity of RA polypeptides against other bacterial strains, including clinical isolated *Helicobacter pylori* strains (B107, J291, J99, J99-AF, J99-A9 and J99-A11) and drug resistant strains (Methicillin-resistant *S. aureus*, NRS382, NRS383, NRS384). Among those *H. pylori* strains, J99-AF, J99-A9 and J99-A11 are clarithromycin resistant strains. The RA polypeptides also showed high antibacterial activity against the clinically isolated strains and even the drug resistant strains. More interestingly, the antimicrobial activity of polypeptide remained stable against DH5α and ATCC12608 in the presence of various salts (physiological concentrations of 150 mM NaCl, 1 mM MgCl$_2$, and 2.5 mM CaCl$_2$), and mucin, the main component of mucosa (Table 2).

TABLE 2

MIC values of PHLG-BIm$_{40}$ in the presence of salts (150 mM NaCl, 1 mM MgCl$_2$, 8 μM CaCl$_2$), human serum (2%), fetal bovine serum (FBS, 5% or 10%), plasma from human (2% or 5%), artificial tear (2%) or mucin (1 mg/mL) against *E. coli* DH5α, and *S. aureus* ATCC12608. Control represents treated with polypeptide only.

| | MIC (μM) | | | | | | | | | | |
|---|---|---|---|---|---|---|---|---|---|---|---|
| Cond. | Control | NaCl | MgCl$_2$ | CaCl$_2$ | 2% Human Serum | 5% FBS | 10% FBS | 2% Plasma | 5% Plasma | 2% Art. tear | Mucin |
| DH5α | 3.3 | 3.3 | 3.3 | 3.3 | 1.5 | 1.5 | 0.7 | 1.5 | 0.7 | 3.3 | 3.3 |
| ATCC 12608 | 13.1 | 13.1 | 13.1 | 6.6 | 6.6 | 6.6 | 3.3 | 6.6 | 3.3 | 6.6 | 13.1 |

The MIC values of RA polypeptide against DH5a and ATCC12608 decreased in the presence of human serum, fetal bovine serum, plasma, and artificial tears in comparison with polypeptide-only treatment. The results demonstrate that the RA polypeptides are stable in serum and plasma, and polyanionic compounds do not dramatically affect their antimicrobial activity. The decreased MIC in serum and plasma may be attributed to the serum complement system, providing innate defense against microbial infections. PHLG-BIm$_{40}$ exhibited low hemolytic activity with an HC50 (50% hemolytic concentration) value higher than 104.6 μM, which indicates a high selectivity of >32 (defined as HC50/MIC), as opposed to a selectivity of >2 for PHDLG-BIm$_{40}$ against DH5a bacterial cells. The polypeptides are not only bacteriostatic but are also bactericidal. Nearly 100% killing of all four bacterial species was observed at their respective MIC or double MIC within 2 h (FIG. 6). In addition, the RA polypeptides showed concentration-dependent antimicrobial killing in medium, and in conditions with NaCl, human serum, plasma, and artificial tears (FIG. 7).

Figure 1H:
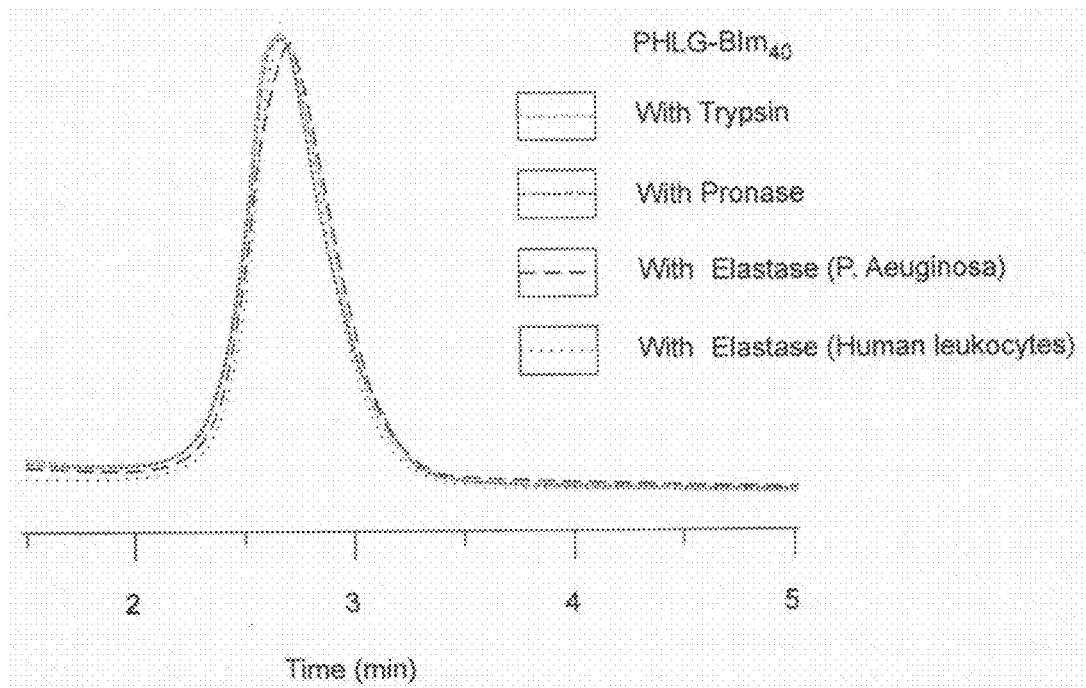
Figure 1I:
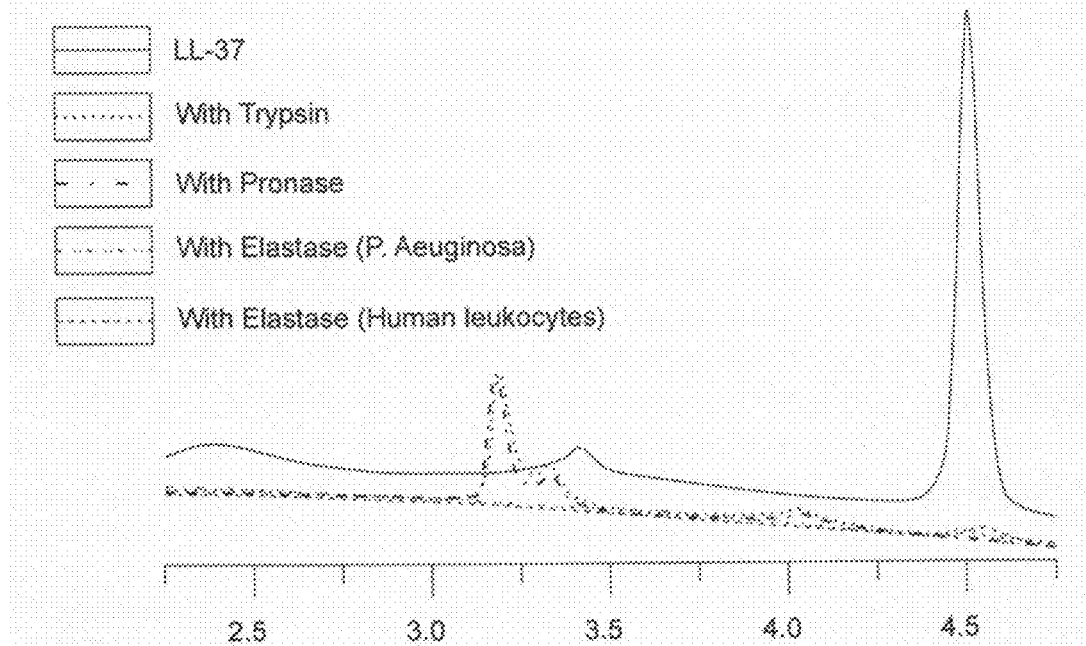

Though many AMPs with high antibacterial activity have been developed, the application of AMPs is usually limited by the short durations of activity due to their rapid digestion by endogenous proteases (Brogden and Brogden (2011) *Int J Antimicrob Agents* 38(3):217-225). The RA polypeptide, with densely packed hydrophobic side chains forming a hydrophobic cortex that can protect the polypeptide backbone amide bonds, in principle should be more stable against proteolysis compared to typical AMPs. We incubated PHLG-BIm$_{40}$ with trypsin, pronase, elastase from *Pseudomonas aeruginosa*, or elastase from human leukocytes for 8 h and analyzed polypeptide degradation by HPLC. PHLG-BIm$_{40}$ exhibited excellent proteolytic stability and experienced almost no degradation against the proteases (FIG. 1H), while LL-37, a positive control AMP, was readily degraded under the same conditions (FIG. 1I). Furthermore, after 8 h of protease or trypsin treatment, the antibacterial activity of PHLG-BIm$_{40}$ remained unchanged, with the same MIC value against DH5a as the untreated polypeptide (3.3 μM).

RA Polypeptide Kills Bacteria by Directly Disrupting the Bacterial Cell Membrane.

Figure 2A:
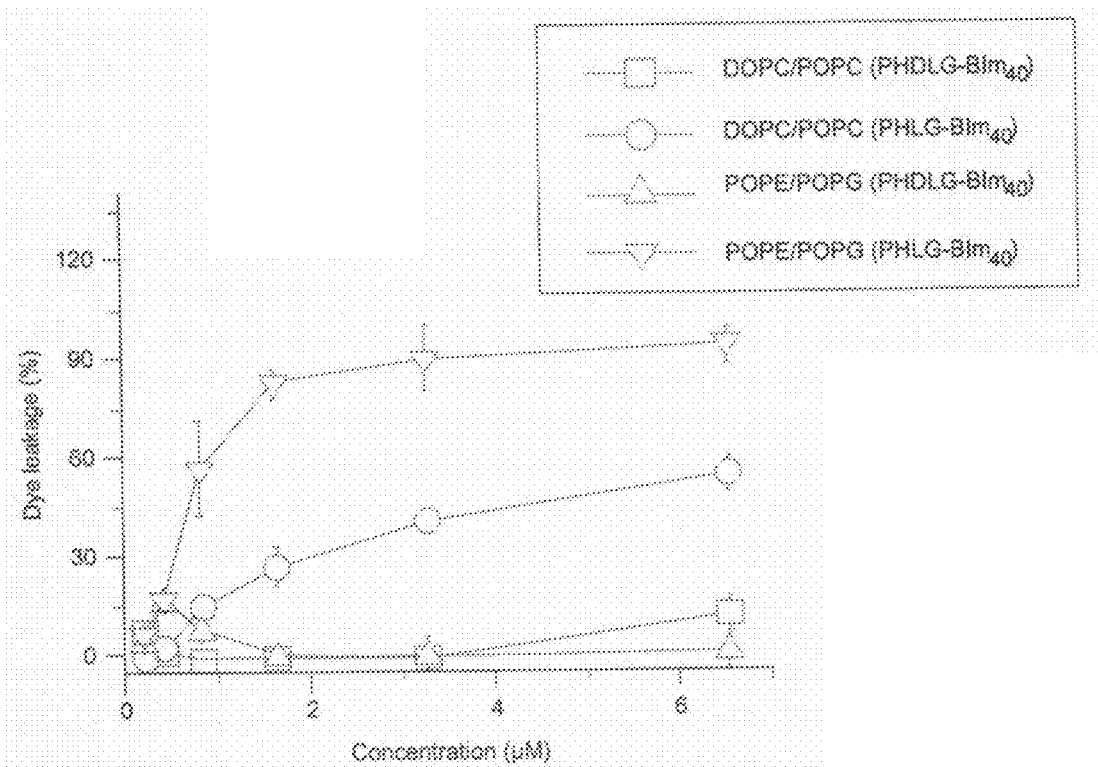
FIG. 2A-D. PHLG-BIm$_{40}$ kills bacteria by directly disrupting the bacterial cell membrane. (a) Extent of calcein efflux in neutral vesicles (DOPC/POPC) and negatively charged vesicles (DOPE/DOPG) after treatment with PHDLG-BIm$_{40}$ (non-helical, lacking radially amphiphilic structure) or PHLG-BIm$_{40}$ (helical with radially amphiphilic structure) at various concentrations for 1 h. (b) Flow cytometry analysis of propidium iodide (PI) uptake after incubation with free PI, PI with PHDLG-BIm$_{40}$ or PI with PHLG-BIm$_{40}$ at various concentrations. All of the data are represented as average±SD and analyzed by student's t-test (**p≤0.01). (c) The fluorescence microscopy of stained *E. coli* MG1655 in the absence and presence of PHDLG-BIm$_{40}$ and PHLG-BIm$_{40}$ (3.3 µM). Bar=50 µm. (d) SEM images of MG1655 after treatment with PBS, PHDLG-BIm$_{40}$ or PHLG-BIm$_{40}$. Bar=1 µm.

We find that the RA PHLG-BIm kills bacteria by directly disrupting the bacterial cell membrane as typical AMPs, through vesicle leakage, bacterial membrane permeabilization, and bacteria morphology assays. We first investigated the membrane-disruptive activity of helical PHLG-BIm$_{40}$ and non-helical PHDLG-BIm$_{40}$ polypeptides on anionic liposomes 1-palmitoyl-2-oleoyl-sn-glycero-3-phosphoethanolamine (POPE)/1-palmitoyl-2-oleoyl-sn-glycero-3-phospho-(1'-rac-glycerol) (POPG) and neutral liposomes 1,2-dioleoyl-sn-glycero-3-phosphocholine (DOPC)/1-palmitoyl-2-oleoyl-sn-glycero-3-phosphocholine (POPC), which were used to model phosphatidylethanolamine (PE) rich bacteria and eukaryotic cell membranes, respectively. At the same concentration, PHLG-BIm$_{40}$ induced greater dye leakage from both anionic and neutral liposomes than PHDLG-BIm$_{40}$, indicating that the helical polypeptide has higher membrane disruption capability (FIG. 2A). PHLG-BIm$_{40}$ also caused more leakage from the anionic liposomes than the neutral liposomes, which is well-correlated with the observed selectivity against bacterial over mammalian cells. The leakage results also showed the capability of PHLG-BIm to permeabilize model bacteria membranes rich in negative intrinsic curvature-forming lipids.

Figure 2B:
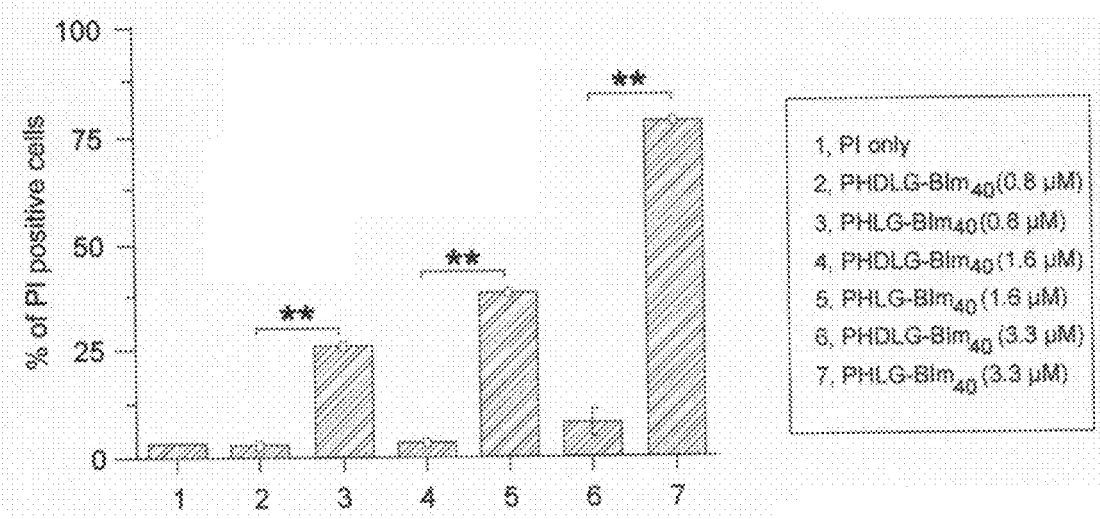
Figure 2C:
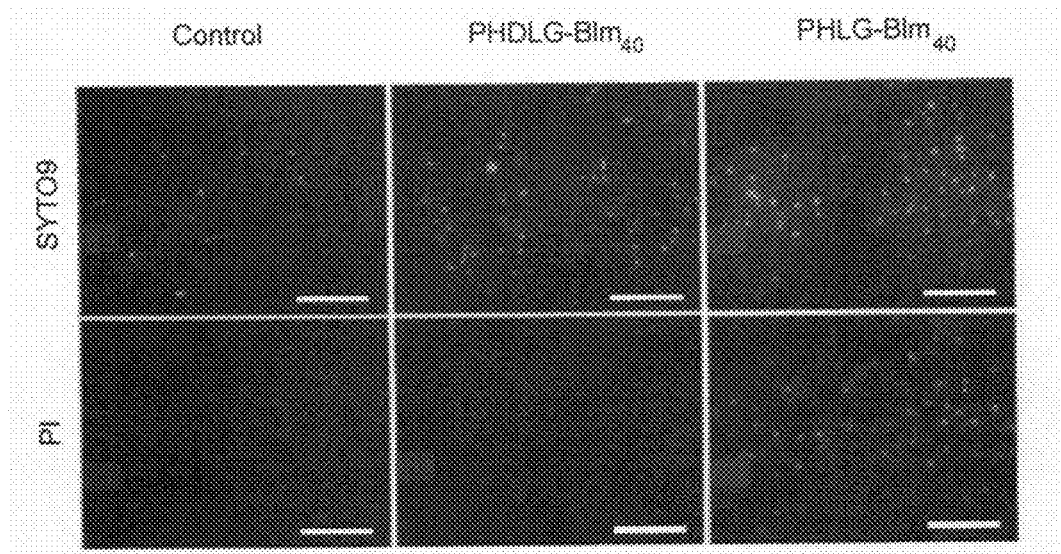
Figure 2D:
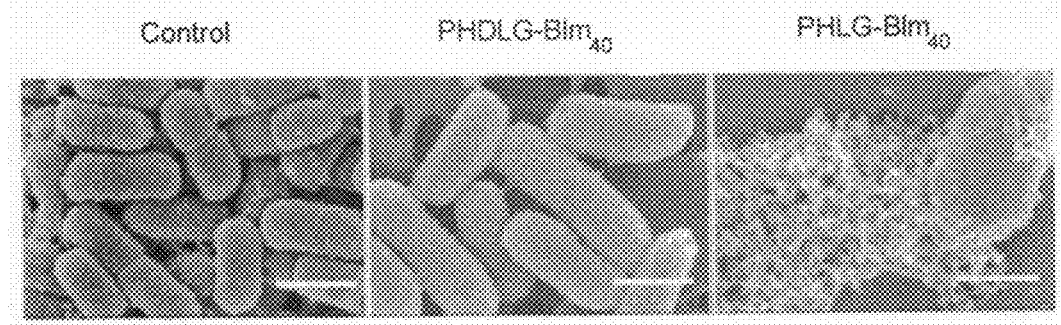

We next used flow cytometry to evaluate permeabilization of PHLG-BIm through bacterial membranes. MG1655 bacteria cells were incubated with PHLG-BIm$_{40}$ and propidium iodide (PI), a membrane impermeable dye. The total number of PI-containing bacteria cells was greater for those treated with PHLG-BIm$_{40}$ than PHDLG-BIm$_{40}$, and increased with higher concentration of polypeptide (FIG. 2B). The uptake study analyzed by fluorescence imaging method provided additional evidence of enhanced membrane activity of PHLG-BIm$_{40}$, which permeabilized MG1655 bacterial cell membranes more effectively than PHDLG-BIm$_{40}$ when the bacterial cells were co-incubated with polypeptide and dye (PI and SYTO9) (FIG. 2C). Using scanning electron microscopy, we observed drastic changes and damage of the bacterial membranes after incubation with PHLG-BIm$_{40}$, while PHDLG-BIm$_{40}$ minimally affected bacteria morphology (FIG. 2D). Taken together, the results indicate that membrane disruption and permeation are an important component of the antimicrobial activity of PHLG-BIm.

To examine in detail the root causes of selective membrane activity for RA polypeptides, we use synchrotron small angle x-ray scattering (SAXS) to investigate the type and quantity of membrane curvature deformations induced by PHLG-BIm. Small unilamellar vesicles (SUVs) were prepared with lipid compositions representative of bacterial (DOPG/DOPE=20/80) and eukaryotic (DOPS/DOPC=20/80) membranes. Compositions DOPG/DOPE/DOPC=20/60/20 and 20/40/40 were also used as model systems to isolate the role of negative intrinsic curvature lipids such as PE, since eukaryotic membranes are known to have lower PE content relative to bacterial membranes.

Figure 3A:
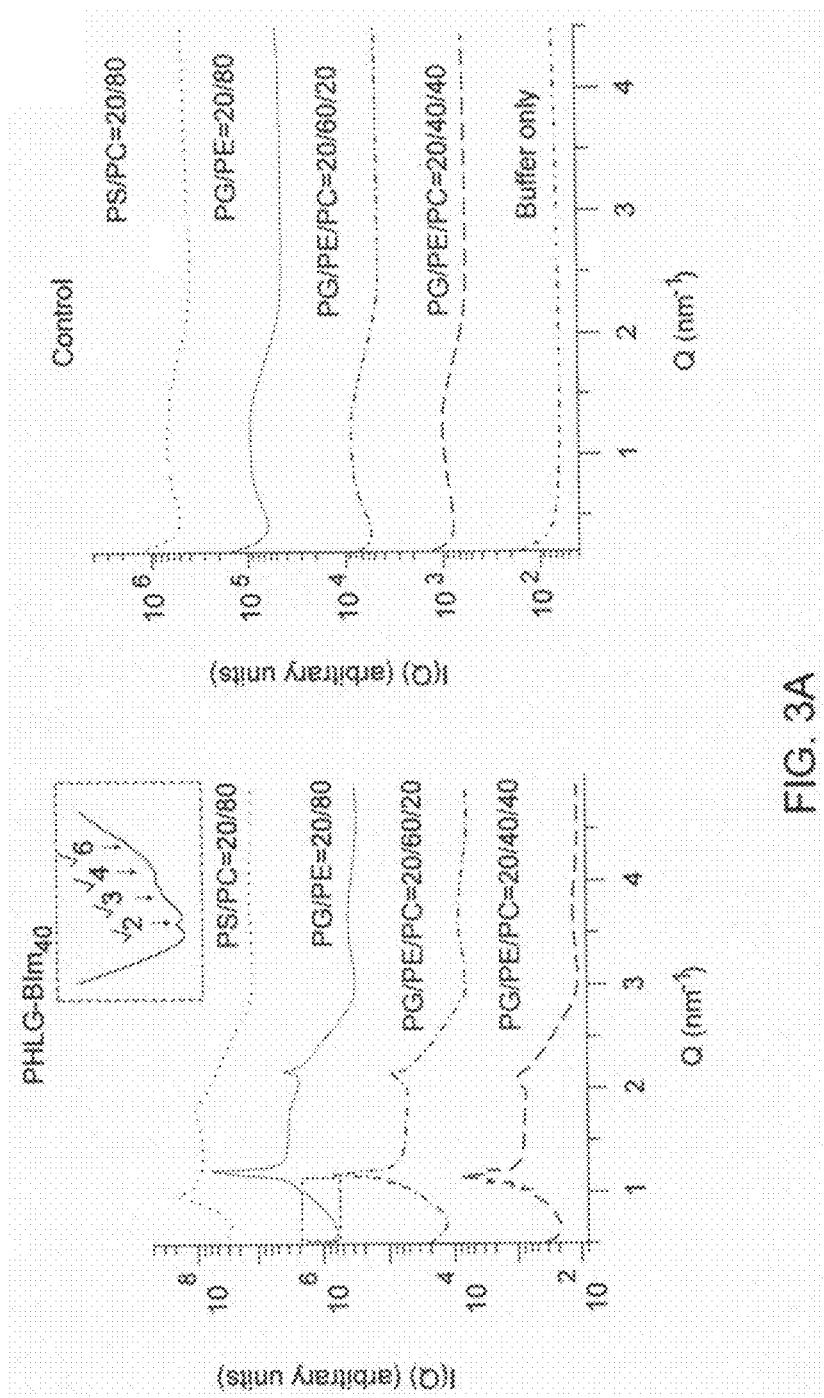
FIG. 3A-B. (a) SAXS spectra show generation of NGC by PHLG-BIm$_{40}$ in membranes rich in PE. SAXS profiles from lipid vesicle solutions after exposure to PHLG-BIm$_{40}$ at molar ratio P/L=1/400. SUV-only controls at each composition show a broad characteristic feature consistent with the form factor of the unilamellar vesicles. (b) PHLG-BIm induces a Pn3m cubic phase. The measured Q positions of the diffraction peaks were plotted to show indexing of the Pn3m cubic phase for DOPG/DOPE=20/80.
Figure 3B:
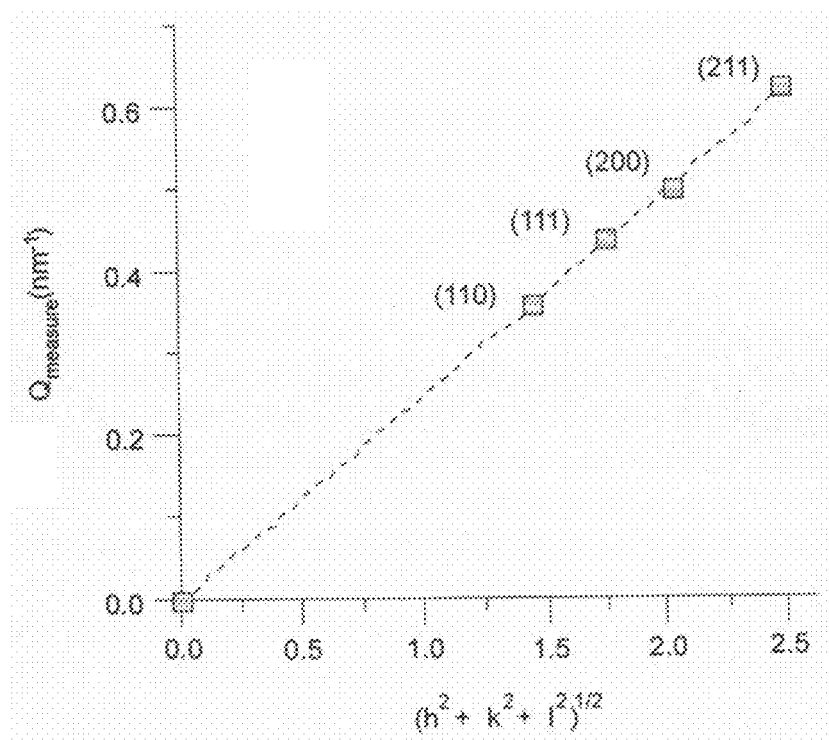

The SUVs were incubated with PHLG-BIm$_{40}$ at a peptide/lipid (P/L) molar ratio of 1/400, which is equivalent to a charge ratio of 1/2, and the resulting structures were characterized using SAXS. Synchrotron SAXS spectra from the lipid vesicle solutions showed a broad characteristic feature consistent with a single lipid bilayer form factor of unilamellar vesicles. When exposed to PHLG-BIm$_{40}$, the lipid vesicles undergo a structural transition, resulting in correlation peaks with specific ratios of Q values in the diffraction data (FIG. 3). For each membrane composition, we found a set of correlation peaks having integral Q-ratios of 1:2 consistent with a lamellar (La) phase, characterized by d-spacings of 6.7-8.8 nm. These lamellar phases resulting from exposure of PHLG-BIm to the SUVs indicate inter-membrane attraction without the generation of significant curvature.

Interestingly, for the model bacterial membrane composition, we identified a second set of correlation peaks with characteristic Q-ratios of $\sqrt{2}:\sqrt{3}:\sqrt{4}:\sqrt{6}$, which indexed to a cubic ($Q_{II}$) Pn3m "double-diamond" lattice having a lattice parameter of 24.8 nm. Bicontinuous cubic phases, such as the Pn3m, consist of two non-intersecting water channels that are separated by a lipid bilayer. The center of this bilayer traces out a minimum surface characterized by negative Gaussian curvature (NGC), also known as saddle splay curvature, at every point. Our SAXS data showed that PHLG-BIm promotes saddle-shaped membrane deformations in model bacteria membranes to stabilize a bulk Pn3m cubic phase. NGC is the saddle-shaped curvature that manifests along the inside of pores, around the base of a bleb, and the neck of a bud, the basic membrane permeation mechanisms. Earlier studies have found a strong correlation between the formation of cubic phases and membrane permeation induced by AMPs (Lee et al. (2014) *Biochim Biophys Acta* 1838(9):2269-2279).

The ability of PHLG-BIm to generate cubic phases in bacteria-like PE-rich membranes indicate that the polypeptide may permeate bacteria membranes via the induction of NGC consistent with that of natural AMPs. By systematically examining a range of membranes, we determined how lipid composition affects the ability of PHLG-BIm to restructure vesicles. We observed the general trend of decreasing PE content resulting in the suppression of non-lamellar phase formation. More specifically, we found that the peptide does not disrupt membranes (no NGC generation) with a PE content of 60% and lower, which includes those representative of eukaryotes. The preference for PHLG-BIm to generate cubic phases at high PE levels of approximately 80% suggests a mechanism of selectivity for bacterial over animal membranes based on their specific lipid distributions, again consistent with generic AMP trends.

RA Polypeptide Enhances the Antibacterial Effects of Traditional Antibiotics.

Because PHLG-BIm can cause membrane disruption and permeabilization, we explored its potential to enhance the antibacterial effect of traditional antibiotics. Synergistic-like enhancement of bacteria-killing has been previously reported from co-administration of membrane-disruptive agents with commercial antibiotics (Ng et al. (2013) *Adv Mater* 25(46):6730-6736). We selected four antibiotics, namely streptomycin (aminoglycoside), doxycycline (tetracycline), rifampicin (rifamycin), and gentamicin (aminoglycoside). Streptomycin, doxycycline, and gentamicin are protein synthesis inhibitors, while rifampicin inhibits DNA-dependent RNA synthesis.

We tested the antibacterial activity of these antibiotics co-administered with helical PHLG-BIm$_{40}$. Non-helical PHDLG-BIm$_{40}$ served as the control. Bacteria were incubated with either antibiotic alone, antibiotic co-administered with PHDLG-BIm$_{40}$, or antibiotic co-administered with PHLG-BIm$_{40}$ at varying concentrations. For MG1655 bacteria, co-administration of streptomycin with PHDLG-BIm$_{40}$ resulted in MIC values identical to those of streptomycin alone (FIG. 4A). However, when streptomycin was co-administered with PHLG-BIm$_{40}$ at concentrations of 1.6, 3.3 and 6.5 µM, the respective MIC values against MG1655 were 2, 133 and 400 times lower than that of streptomycin alone. Because the MIC against MG1655 with PHLG-BIm$_{40}$ alone was 26.1 µM, this result suggested a synergistic effect from combining treatments of streptomycin and PHLG-BIm$_{40}$. We also observed a similar synergistic effect of PHLG-BIm$_{40}$ and antibiotics against C101 (*P. aeruginosa*), a bacterium with high resistance to many antibiotics. For C101 bacteria, the MIC of PHLG-BIm alone was 52.3 µM. A synergistic effect when streptomycin was co-administered with PHLG-BIm$_{40}$ (13.1 µM) was indicated by an MIC that was 128 times lower than that of streptomycin alone (FIG. 4B). The synergistic effect of combination therapy was also detected against three other bacterial strains, DH5α, ATCC11778, and ATCC12608 (Table 3) and three other antibiotics: doxycycline, rifampicin, and gentamicin (Table 4).

TABLE 3

The Antimicrobial Activity of Streptomycin Co-administered with PHLG-BIm or PHDLG-BIm at Various Concentrations against DH5α (MIC of PHLG-BIm: 3.3 µM), ATCC11778 (MIC PHLG-BIm: 26.1 µM) and ATCC12608 (MIC PHLG-BIm: 26.1 µM).

| Polypeptide | MIC (DH5α, µM, ΣFIC$^a$) | MIC (ATCC11778, µM, ΣFIC$^a$) | MIC (ATCC12608, µM, ΣFIC$^a$) |
|---|---|---|---|
| Without polypeptide | 6.9 | 6.9 | 6.9 |
| With PHDLG-BIm$_{40}$ (1.6 µM) | 6.9 (1.5) | 6.9 (1.1) | 6.9 (1.1) |
| With PHLG-BIm$_{40}$ (0.8 µM) | 1.7 (0.5) | 1.7 (0.3) | 3.4 (0.6) |
| With PHLG-BIm$_{40}$ (1.6 µM) | 0.05 (0.5) | 0.4 (0.2) | 0.05 (0.1) |

TABLE 4

The Antimicrobial Activity of Various Antibiotics Co-administered with PHLG-BIm (3.3 µM) or PHDLG-BIm (3.3 µM) against MG1655 (MIC of PHLG-BIm: 26.1 µM) and C101 (MIC PHLG-BIm: 52.3 µM).

| Bacteria | Polypeptide | MIC (Doxycycline, µM, ΣFIC) | MIC (Rifampicin, µM, ΣFIC) | MIC (Gentamicin, µM, ΣFIC) |
|---|---|---|---|---|
| MG1655 | Without polypeptide | 4.5 | 9.7 | 2.1 |
|  | With PHLG-BIm$_{40}$ | 0.6 (0.2) | 0.125 (0.1) | 0.5 (0.4) |
|  | With PHDLG-BIm$_{40}$ | 4.5 (1.1) | 0.2 (1.1) | 2.1 (1.1) |
| C101 | Without polypeptide | 288.0 | 77.8 | 8.4 |
|  | With PHLG-BIm$_{40}$ | 3.6 (0.2) | 2.4 (0.2) | 1.0 (0.2) |
|  | With PHDLG-BIm$_{40}$ | 288.0 (1.1) | 77.8 (1.1) | 8.4 (1.1) |

For Tables 3 and 4: $^a$ΣFIC=MIC$_{A,combination}$/MIC$_{A,alone}$+MIC$_{B,combination}$/MIC$_{B,alone}$. Synergy is defined as ΣFIC index≤0.5. Indifference was defined as ΣFIC index of >0.5 but ≤4. Antagonism was defined as ΣFIC index>4.0.

The synergistic effect of the combination therapy is likely a result of enhanced antibiotic uptake due to polypeptide-induced membrane permeation. To test this hypothesis, bacterial cells were incubated with rifampicin without or with polypeptides. After 0.5 h or 1 h incubation with RA polypeptide, we observed increased intracellular uptake of rifampicin in MG1655 and C101 cells (FIG. 8). These findings indicate that the synergy from co-administering antibiotics with RA-polypeptides results from increased antibiotic uptake, such as that caused by peptide-induced defects, or suppressed efflux activities. Our study showed combination therapy to be a promising application for this class of membrane-active RA polypeptides, which can significantly improve the effectiveness of traditional commercial antibiotics by killing bacteria through a distinct mode of action.

Combination Therapy

The antibacterial polypeptides described herein may be administered alone or in combination with other therapeutic agents, such as antibiotic, anti-inflammatory or antiseptic agents such as anti-bacterial agents, anti-fungicides, anti-viral agents, and anti-parasitic agents. In some embodiments, a pharmaceutical composition comprises one or more antibacterial polypeptides described herein and one or more antibiotic or antiseptic agents. Examples of suitable active agents include penicillins, cephalosporins, carbacephems, cephamycins, carbapenems, monobactams, aminoglycosides, glycopeptides, quinolones, tetracyclines, macrolides, and fluoroquinolones. Suitable antiseptic agents that can be used include iodine, silver, copper, chlorhexidine, polyhexanide and other biguanides, chitosan, acetic acid, and hydrogen peroxide. These agents may be incorporated as part of the same pharmaceutical composition or may be administered separately (concurrently or sequentially). The pharmaceutical compositions may also contain anti-inflammatory drugs such as steroids and macrolactam derivatives.

Several embodiments described herein relate to a pharmaceutical composition that includes one or more β-lactam antibiotics and one or more antibacterial polypeptides described herein. β-Lactam antibiotics are bactericidal, and can act by inhibiting the synthesis of the peptidoglycan layer of bacterial cell walls. The peptidoglycan layer is important for cell wall structural integrity, especially in Gram-positive bacteria. Examples of β-lactam antibiotics include, but are not limited to, benzathine penicillin, benzylpenicillin (penicillin G), phenoxymethylpenicillin (penicillin V), procaine penicillin, methicillin, oxacillin, nafcillin, cloxacillin, dicloxacillin, flucloxacillin, temocillin, amoxicillin, ampicillin, co-amoxiclav, azlocillin, carbenicillin, ticarcillin, mezlocillin, piperacillin, cephalosporins, cephalexin, cephalothin, cefazolin, cefaclor, ceftaroline, cefuroxime, cefamandole, cephamycins, cefotetan, cefoxitin, ceftriaxone, cefotaxime, cefpodoxime, cefixime, ceftazidime, cefepime, cefpirome, imipenem, meropenem, ertapenem, faropenem, doripenem, monobactams, aztreonam, tigemonam, nocardicin A, and tabtoxinine-β-lactam.

Embodiments of the invention include methods for inhibiting the growth and/or reproduction of susceptible organisms, and/or to increasing the sensitivity of susceptible organisms to antibiotics by administering them in combination (concurrently or sequentially) with an antibacterial polypeptide described herein. Susceptible organisms generally include Gram-positive and Gram-negative, aerobic and anaerobic organisms whose growth can be inhibited by embodiments described herein. Susceptible organisms include, but are not limited to, *Staphylococcus, Lactobacillus, Streptococcus, Streptococcus agalactiae, Sarcina, S. pneumoniae, S. pyogenes, S. mutans, Escherichia, Enterobacter, Klebsiella, Pseudomonas, Pseudomonas aeruginosa, Acinetobacter, Proteus, Campylobacter, Citrobacter, Nisseria, Bacillus anthracis, Bacillus cereus, Bacillus subtilis, Bacteroides, Peptococcus, Clostridium, Salmonella, Shigella, Serratia, Haemophilus, Brucella, Mycobacterium tuberculosis* and similar organisms.

Pharmaceutical Formulations

The compounds described herein can be used to prepare therapeutic pharmaceutical compositions, for example, by combining the compounds with a pharmaceutically acceptable diluent, excipient, or carrier. The compounds may be added to a carrier in the form of a salt or solvate. For example, in cases where compounds are sufficiently basic or acidic to form stable nontoxic acid or base salts, administration of the compounds as salts may be appropriate.

Examples of pharmaceutically acceptable salts are organic acid addition salts formed with acids that form a physiological acceptable anion, for example, tosylate, methanesulfonate, acetate, citrate, malonate, tartrate, succinate, benzoate, ascorbate, α-ketoglutarate, and β-glycerophosphate. Suitable inorganic salts may also be formed, including hydrochloride, halide, sulfate, nitrate, bicarbonate, and carbonate salts.

Pharmaceutically acceptable salts may be obtained using standard procedures well known in the art, for example by reacting a sufficiently basic compound such as an amine with a suitable acid to provide a physiologically acceptable ionic compound. Alkali metal (for example, sodium, potassium or lithium) or alkaline earth metal (for example, calcium) salts of carboxylic acids can also be prepared by analogous methods.

The compounds of the formulas described herein can be formulated as pharmaceutical compositions and administered to a mammalian host, such as a human patient, in a variety of forms. The forms can be specifically adapted to a chosen route of administration, e.g., oral or parenteral administration, by intravenous, intramuscular, topical or subcutaneous routes.

The compounds described herein may be systemically administered in combination with a pharmaceutically acceptable vehicle, such as an inert diluent or an assimilable edible carrier. For oral administration, compounds can be enclosed in hard or soft shell gelatin capsules, compressed into tablets, or incorporated directly into the food of a patient's diet. Compounds may also be combined with one or more excipients and used in the form of ingestible tablets, buccal tablets, troches, capsules, elixirs, suspensions, syrups, wafers, and the like. Such compositions and preparations typically contain at least 0.1% of active compound. The percentage of the compositions and preparations can vary and may conveniently be from about 0.5% to about 60%, about 1% to about 25%, or about 2% to about 10%, of the weight of a given unit dosage form. The amount of active compound in such therapeutically useful compositions can be such that an effective dosage level can be obtained.

The tablets, troches, pills, capsules, and the like may also contain one or more of the following: binders such as gum tragacanth, acacia, corn starch or gelatin; excipients such as dicalcium phosphate; a disintegrating agent such as corn starch, potato starch, alginic acid and the like; and a lubricant such as magnesium stearate. A sweetening agent such as sucrose, fructose, lactose or aspartame; or a flavoring agent such as peppermint, oil of wintergreen, or cherry flavoring, may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propyl parabens as preservatives, a dye and flavoring such as cherry or orange flavor. Any material used in preparing any unit dosage form should be pharmaceutically acceptable and substantially non-toxic in the amounts employed. In addition, the active compound may be incorporated into sustained-release preparations and devices.

The active compound may be administered intravenously or intraperitoneally by infusion or injection. Solutions of the active compound or its salts can be prepared in water, optionally mixed with a nontoxic surfactant. Dispersions can be prepared in glycerol, liquid polyethylene glycols, triacetin, or mixtures thereof, or in a pharmaceutically acceptable oil. Under ordinary conditions of storage and use, preparations may contain a preservative to prevent the growth of microorganisms.

Pharmaceutical dosage forms suitable for injection or infusion can include sterile aqueous solutions, dispersions, or sterile powders comprising the active ingredient adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions, or by the use of surfactants. The prevention of the action of microorganisms can be brought about by various antibacterial and/or antifungal agents, for example, parabens, chlorobutanol, phenol, sorbic acid, thimerosal, and the like. In many cases, it will be preferable to include isotonic agents, for example, sugars, buffers, or sodium chloride. Prolonged absorption of the injectable compositions can be brought about by agents delaying absorption, for example, aluminum monostearate and/or gelatin.

Sterile injectable solutions can be prepared by incorporating the active compound in the required amount in the appropriate solvent with various other ingredients enumerated above, as required, optionally followed by filter sterilization. In the case of sterile powders for the preparation of sterile injectable solutions, methods of preparation can include vacuum drying and freeze drying techniques, which yield a powder of the active ingredient plus any additional desired ingredient present in the solution.

For topical administration, compounds may be applied in pure form, e.g., when they are liquids. However, it will generally be desirable to administer the active agent to the skin as a composition or formulation, for example, in combination with a dermatologically acceptable carrier, which may be a solid, a liquid, a gel, or the like.

Useful solid carriers include finely divided solids such as talc, clay, microcrystalline cellulose, silica, alumina, and the like. Useful liquid carriers include water, dimethyl sulfoxide (DMSO), alcohols, glycols, or water-alcohol/glycol blends, in which a compound can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using a pump-type or aerosol sprayer.

Thickeners such as synthetic polymers, fatty acids, fatty acid salts and esters, fatty alcohols, modified celluloses, or modified mineral materials can also be employed with liquid carriers to form spreadable pastes, gels, ointments, soaps, and the like, for application directly to the skin of the user.

Examples of dermatological compositions for delivering active agents to the skin are known to the art; for example, see U.S. Pat. No. 4,992,478 (Geria), U.S. Pat. No. 4,820,508 (Wortzman), U.S. Pat. No. 4,608,392 (Jacquet et al.), and U.S. Pat. No. 4,559,157 (Smith et al.). Such dermatological compositions can be used in combinations with the compounds described herein where an ingredient of such compositions can optionally be replaced by a compound described herein, or a compound described herein can be added to the composition.

Useful dosages of the compounds (e.g., the peptides) described herein can be determined by comparing their in vitro activity, and in vivo activity in animal models. Methods for the extrapolation of effective dosages in mice, and other animals, to humans are known to the art; for example, see U.S. Pat. No. 4,938,949 (Borch et al.). The amount of a compound, or an active salt or derivative thereof, required for use in treatment will vary not only with the particular compound or salt selected but also with the route of administration, the nature of the condition being treated, and the age and condition of the patient, and will be ultimately at the discretion of an attendant physician or clinician.

The compound can be conveniently administered in a unit dosage form, for example, containing 5 to 1000 $mg/m^2$, conveniently 10 to 750 $mg/m^2$, most conveniently, 50 to 500 $mg/m^2$ of active ingredient per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Materials.

Chemicals were purchased from Sigma-Aldrich (St. Louis, Mo., USA) and used as received unless otherwise specified. Anhydrous dimethylformamide (DMF), ethyl acetate (EtOAc), and hexane were dried by passing them through alumina columns and kept anhydrous by storing them in the presence of molecular sieves in a glove box. Hexamethyldisilazane (HMDS) was dissolved in DMF in a glovebox. SiliaFlash P60 silica gel (particle size 40-63 μm) was purchased from SiliCycle Inc. (Quebec City, Quebec, Canada) and heated to 150° C. for 48 h before use. Spectra/Por® dialysis tubing with a molecular weight cut-off (MWCO) of 1 kDa was purchased from Spectrum Laboratories (Rancho Dominguez, Calif., USA).

Gram-negative bacteria, DH5α (*Escherichia coli*), MG1655 (*E. coli*), C101 (*Pseudomonas aeruginosa*), and Gram-positive bacteria, ATCC12608 (*Staphylococcus aureus*) and ATCC11778 (*Bacillus toyonensis*) were grown in luria broth (LB) medium at 37° C. Clinical isolated

*Helicobacter pylori* strains, B107, J291, J99, J99-AF, J99-A9 and J99-A11 were incubated in *brucella* broth (BB) with 10% fetal bovine serum (FBS) supplemented with vancomycin (5 µg/mL) at 37° C. Among them, J99-AF, J99-A9 and J99-A11 are drug resistant bacteria. All lipids were obtained from Avanti Polar Lipids, Inc. Propidium iodide (PI) and BacLight™ Kit L-7012 was purchased from Thermo Fisher Scientific Inc. Artificial tears were obtained from Boss Safety Products. *Pseudomonas Aeruginosa* Elastase was purchased from Elastin Products Company, Inc. LL-37 (see Dun et al. (2006) *Biochim Biophys Acta* 1758(9):1408-1425; Stromstedt et al. (2009) *Antimicrob Agents Chemother* 53(2):593-602) was obtained from AnaSpec, Inc. Elastase from human leukocytes, plasma from human, human serum was obtained from Sigma-Aldrich.

Characterization.

$^{1}$H NMR spectra were recorded on a Varian U500 MHz or a VXR-500 MHz spectrometer. $^{13}$C-$^{1}$H HSQC (heteronuclear single quantum coherence) NMR, $^{1}$H-$^{1}$H TOCSY (total correlation spectroscopy) NMR, and NOESY (nuclear overhauser effect spectroscopy, the mixing time is 150 ms) NMR were recorded on a VNS750NB spectrometer. Chemical shifts were reported in ppm and referenced to the solvent proton impurities. The molecular weights of prepared polypeptides were determined by gel permeation chromatography (GPC) equipped with an isocratic pump (Model 1100, Agilent Technology, Santa Clara, Calif., USA), a DAWN HELEOS multi-angle laser light scattering detector (MALLS) detector (Wyatt Technology, Santa Barbara, Calif., USA), and an OptilabrEX refractive index detector (Wyatt Technology, Santa Barbara, Calif., USA). The detection wavelength of HELEOS was set at 658 nm. Separations were performed using serially connected size exclusion columns (100 Å, 500 Å, 10$^3$ Å and 10$^4$ Å Phenogel columns, 5 µm, 300×7.8 mm, Phenomenex, Torrance, Calif., USA) at 60° C. using DMF containing 0.1 mol/L LiBr as the mobile phase. The MALLS detector was calibrated using pure toluene and can be used for determination of the absolute molecular weights (MWs). The MWs of polymers were determined based on the do/dc value of each polymer sample calculated offline by using the internal calibration system processed by the ASTRA V software (version 5.1.7.3, Wyatt Technology, Santa Barbara, Calif., USA).

Circular dichroism (CD) measurements were carried out on a JASCO J-815 CD spectrometer. The polypeptides samples were prepared at concentrations of 0.40 mg/mL in water, and placed in a quartz cell with a pathlength of 0.10 cm prior to measurements. Infrared spectra were recorded on a Perkin Elmer 100 serial FTIR spectrophotometer calibrated with polystyrene film. Lyophilization was conducted in a FreeZonelyophilizer (Labconco, Kansas City, Mo., USA). HPLC analyses were performed on a Shimadzu CBM-20A system (Shimadzu, Kyoto, Japan) equipped with SPD20A PDA detector (190 nm-800 nm) and RF10Ax1 fluorescence detector, and an analytical C18 column (Shimadzu, 3 µm, 50×4.6 mm, Kyoto, Japan).

Example 1. Preparation of Helical Polypeptides with Radial Amphiphilicity

Helical polypeptides with radial amphiphilicity display highly selective antimicrobial activity. The RA helical polypeptides and their non-helical counterparts can be prepared as described below, for example, as show in Scheme 1-1.

Scheme 1-1. Synthesis of antibacterial PHLG-based polypeptides

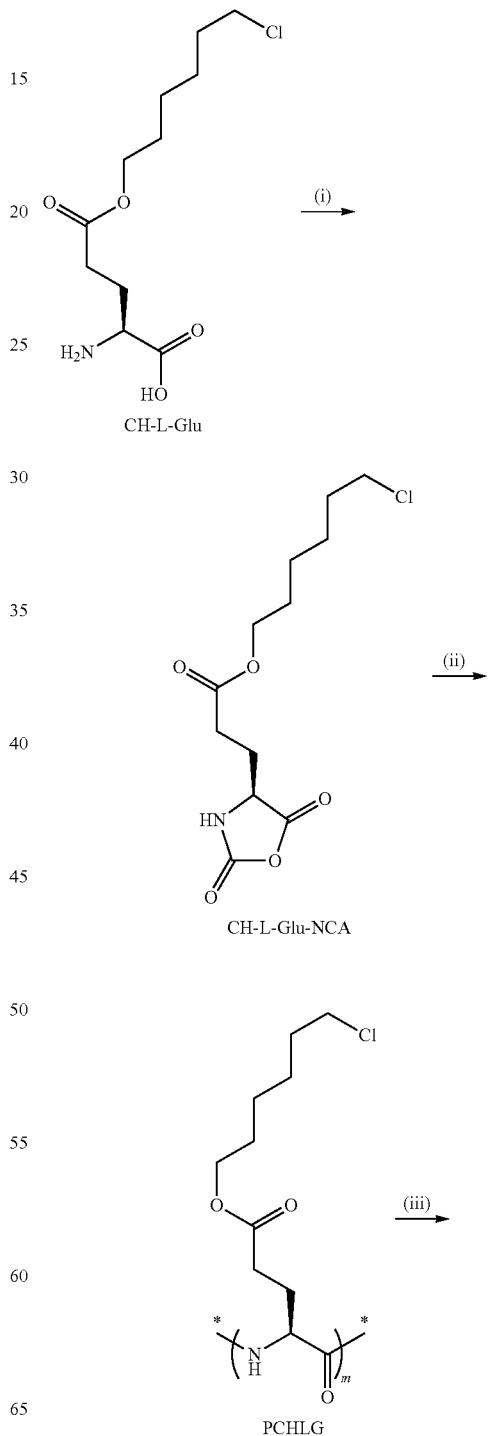

-continued

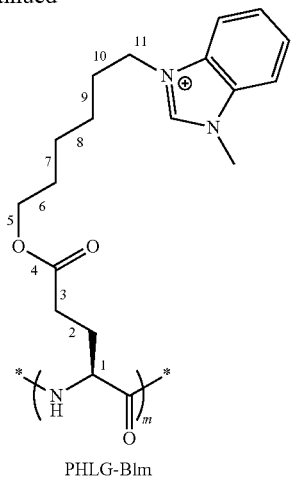

PHLG-BIm (i) phosgene; (ii) HDMS/DMF; (iii) tertiary amine (e.g., 1-methylbenzimidazole (BIm)), NaI, DMF/MeCN With long hydrophobic side chains, the cationic polypeptides exhibit stable helical structures. These polypeptides have isotropic helical structure with the hydrophobic segments of the side chains bundled together to form the interior part of the cylindrical-shaped helix shielded by the exterior cationic charge on/near the surfaces of the helix.

Synthesis of γ-(6-Chlorohexyl)-L-Glutamate (CH-L-Glu).

L-Glutamic acid (10.0 g, 68.0 mmol) and 6-chlorohexanol (15 mL, 112.4 mmol) were mixed and stirred at 0° C., followed by the dropwise addition of $H_2SO_4$ (4 mL). The reaction was allowed to warm up to the room temperature and kept stirred for 24 h. Saturated $Na_2CO_3$ solution was then added to adjust the pH value to 7. The resulting precipitate was collected by filtration and purified by recrystallization from isopropanol/$H_2O$ (1:1, v/v). Isopropanol was removed under vacuum and water was removed via lyophilization to obtain a white solid powder (6.92 g, yield: 38%). $^1$H NMR (DMSO:DCl-$D_2O$, 9:1, v/v): δ 3.91 (t, 2H, —CH$_2$OOC—), 3.82 (t, 1H, α-H), 3.52 (t, 2H, —CH$_2$Cl), 2.53-2.32 (m, 2H, —CH$_2$CH$_2$COO—), 1.98 (m, 2H, —CH$_2$CH$_2$COO—), 1.64-1.17 (m, 8H, ClCH$_2$(CH$_2$)$_4$CH$_2$O—).

CH-DL-Glu was synthesized similarly using DL-glutamic acid as the starting material (Yield: 36%). $^1$H NMR (DMSO:DCl-$D_2O$, 9:1, v/v): 3.91 (t, 2H, —CH$_2$OOC—), 3.82 (t, 1H, α-H), 3.52 (t, 2H, —CH$_2$Cl), 2.53-2.32 (m, 2H, —CH$_2$CH$_2$COO—), 1.98 (m, 2H, —CH$_2$CH$_2$COO—), 1.64-1.17 (m, 8H, ClCH$_2$(CH$_2$)$_4$CH$_2$O—).

Synthesis of CH-L-Glu Based N-Carboxyanhydride (CH-L-Glu-NCA).

A round-bottomed flask (100 mL) was charged with CH-L-Glu (7.3 g, 27.4 mmol) and dried under vacuum for 2 h. Anhydrous tetrahydrofuran (THF, 60 mL) and phosgene (15 wt % in toluene, 39.2 mL, 54.9 mmol) were added successively with the protection of nitrogen. The mixture was stirred at 50° C. for 2 h. The solvent was removed under vacuum to yield an oily liquid. The product was purified by silica gel column chromatography using EtOAC/hexane (from 100% to 60% hexanes) as the eluent (6.6 g, yield: 83%). $^1$H NMR (CDCl$_3$, ppm): δ 7.16 (s, 1H, —NH), 4.43 (t, 1H, —CHNH), 4.05 (t, 2H, —CH$_2$OOC—), 3.51 (t, 2H, —CH$_2$Cl), 2.51 (t, 2H, —CH$_2$CH$_2$COO—), 2.25-2.07 (m, 2H, —CH$_2$CH$_2$COO—), 1.79-1.30 (m, 8H, ClCH$_2$(CH$_2$)$_4$CH$_2$O—). $^{13}$C NMR (CDCl$_3$, ppm): δ 172.8, 170.0, 152.6, 65.4, 57.1, 45.2, 32.6, 29.7, 28.5, 27.0, 26.6, 25.4.

CH-DL-Glu-NCA was synthesized similarly using CH-DL-Glu as the starting material (Yield: 79%). $^1$H NMR (CDCl$_3$, ppm): δ 7.31 (s, 1H, —NH), 4.41 (s, 1H, —CHNH), 3.99 (s, 2H, —CH$_2$OOC—), 3.45 (s, 2H, —CH$_2$Cl), 2.45 (s, 2H, —CH$_2$CH$_2$COO—), 2.10 (d, 2H, —CH$_2$CH$_2$COO—), 1.75-1.22 (m, 8H, ClCH$_2$(CH$_2$)$_4$CH$_2$O—). $^{13}$C NMR (CDCl$_3$, ppm): δ 172.8, 170.2, 152.7, 65.3, 57.1, 45.3, 32.5, 29.6, 28.5, 27.0, 26.6, 25.3.

Synthesis of Poly(γ-6-Chlorohexyl-L-Glutamate) (PCHLG).

In a glovebox, CH-L-Glu NCA (100 mg, 0.34 mmol) was dissolved in DMF (1.5 mL), followed by the addition of 85 µL or 136 µL HMDS (0.1 M) in DMF to obtain PCHLG$_{40}$ and PCHLG$_{28}$. The mixture was stirred at room temperature for 48 h. The polymer was then obtained by precipitation in cold methanol and dried under vacuum at 40° C. for 8 h (Yield: PCHLG$_{40}$: 66%, PCHLG$_{28}$: 56%). $^1$H NMR (CDCl$_3$:TFA-d, 85:15, v/v): DP=40: δ 4.60 (m, 1H, —CHNH), 4.09 (m, 2H, —CH$_2$OOC—), 3.52 (t, 2H, —CH$_2$Cl), 2.50 (m, 2H, —CH$_2$CH$_2$COO—), 2.19-1.90 (m, 2H, —CH$_2$CH$_2$COO—), 1.81-1.30 (m, 8H, ClCH$_2$(CH$_2$)$_4$CH$_2$O—). DP=25 δ 4.60 (m, 1H, —CHNH), 4.09 (m, 2H, —CH$_2$OOC—), 3.52 (t, 2H, —CH$_2$Cl), 2.50 (m, 2H, —CH$_2$CH$_2$COO—), 2.19-1.90 (m, 2H, —CH$_2$CH$_2$COO—), 1.81-1.30 (m, 8H, ClCH$_2$(CH$_2$)$_4$CH$_2$O—).

PCHDLG$_{40}$ was synthesized similarly using CH-DL-Glu-NCA as the monomer (M/I=40) (Yield: 72%). $^1$H NMR (CDCl$_3$/TFA-d, 85:15, v/v): δ 4.60 (m, 1H, —CHNH), 4.10 (m, 2H, —CH$_2$OOC—), 3.52 (t, 2H, —CH$_2$Cl), 2.48 (s, 2H, —CH$_2$CH$_2$COO—), 2.28-1.90 (m, 2H, —CH$_2$CH$_2$COO—), 1.81-1.30 (m, 8H, ClCH$_2$(CH$_2$)$_4$CH$_2$O—).

Synthesis of PHLG-BIm Polypeptides.

PCHLG$_{40}$ (86.5 mg, 0.35 mmol of Cl groups) in DMF (2 mL) and NaI (157 mg, 1.05 mmol) in acetonitrile (2 mL) was mixed and added to 1-methylbenzimidazole (92.4 mg, 0.70 mmol) in a 25 mL Schlenk tube. The mixture was stirred at 80° C. for 48 h. After most solvent was removed under vacuum, NaCl aqueous solution (1.0 M, 3 mL) was added. The solution was then stirred at room temperature for 3 h to promote ion exchange. The product was purified by dialysis (MWCO=1 kDa) against distilled water for 3 days. White solid powder was obtained after lyophilization (yield: 62%). $^1$H NMR (TFA-d): δ 9.02 (s, 1H, —NCHN—), 7.86 (m, 4H, Ar—H), 4.86 (s, 1H, α-H), 4.36 (m, 2H, —COOCH$_2$(CH$_2$)$_4$CH$_2$N—), 4.29 (s, 2H, —COOCH$_2$(CH$_2$)$_4$CH$_2$N—), 4.24 (s, 3H, —NCH$_3$), 2.72 (s, 2H, —CH$_2$CH$_2$COO—), 2.46-1.75 (m, 6H, —CH$_2$CH$_2$COO— and —COOCH$_2$CH$_2$CH$_2$CH$_2$CH$_2$CH$_2$N—), 1.59 (s, 4H, —COOCH$_2$CH$_2$CH$_2$CH$_2$CH$_2$CH$_2$N—).

PHDLG-BIm$_{40}$ was synthesized similarly using PCHDLG$_{40}$ as the starting material. $^1$H NMR (D$_2$O): δ 7.71 (s, 1H, —NCHN—), 7.52 (m, 4H, Ar—H), 4.66 (s, 1H, α-H), 4.36 (m, 2H, —COOCH$_2$(CH$_2$)$_4$CH$_2$N—), 3.89 (s, 3H, —NCH$_3$), 3.74 (s, 2H, —COOCH$_2$(CH$_2$)$_4$CH$_2$N—), 2.32 (s, 2H, —CH$_2$CH$_2$COO—), 2.16-1.75 (m, 4H, —CH$_2$CH$_2$COO— and —COOCH$_2$CH$_2$CH$_2$CH$_2$CH$_2$CH$_2$N—), 1.49-0.89 (s, 6H, —COOCH$_2$CH$_2$CH$_2$CH$_2$CH$_2$CH$_2$N—).

PHLG-BIm$_{28}$ was synthesized similarly using PCHLG$_{28}$ as the starting material. $^1$H NMR (TFA-d): δ 9.02 (s, 1H, —NCHN—), 7.86 (m, 4H, Ar—H), 4.86 (s, 1H, α-H), 4.36 (m, 2H, —COOCH$_2$(CH$_2$)$_4$CH$_2$N—), 4.29 (s, 2H, —COOCH$_2$(CH$_2$)$_4$CH$_2$N—), 4.24 (s, 3H, —NCH$_3$), 2.72 (s, 2H, —CH$_2$CH$_2$COO—), 2.46-1.75 (m, 6H, —CH$_2$CH$_2$COO— and —COOCH$_2$CH$_2$CH$_2$CH$_2$CH$_2$N—), 1.59 (s, 4H, —COOCH$_2$CH$_2$CH$_2$CH$_2$CH$_2$N—).

TABLE 1-1

Data from Synthesis of Polypeptides with Chloroalkyl Side Chains.[a]

| Polypeptide | Monomer | M/I | M$_n$ (kDa)[b] | M$_w$/M$_n$[b] |
|---|---|---|---|---|
| PCHLG$_{40}$ | CH-L-glu-NCA | 40/1 | 10.0 | 1.02 |
| PCHDLG$_{40}$ | CH-DL-glu-NCA | 40/1 | 9.7 | 1.10 |
| PCHLG$_{28}$ | CH-L-glu-NCA | 25/1 | 7.0 | 1.21 |

[a] Polymerizations were carried at room temperature for 48 h. Monomer conversions were all above 99%.
[b] Determined by GPC.

Example 2. Analysis and Characterization of Polypeptides with Radial Amphiphilicity The antimicrobial activity of the polypeptides described herein was analyzed according to the following methods. Helical polypeptides with radial amphiphilicity were found to display highly selective antimicrobial activity.

Simulation Methods.

We conducted molecular dynamics simulations of PHLG-BIm with a DP of 20 following a procedure similar to that of Mansbach and Ferguson (2015) J Chem Phys 142, 105101. The non-natural peptide side chains were constructed using the Automated Topology Builder (ATB) server (compbio.biosci.uq.edu.au/atb/) (see Koziara et al. (2014) J Comput Aid Mol Des 28(3):221-233) to define the structure, partial charges, and bonded and non-bonded interactions within the GROMOS 54A7 force field (see Schmid et al. (2011) Eur Biophys J 40(7):843-856). The peptide backbone was initialized in a α-helical conformation with the assistance of the Bax Group PDB Utility Server (spin-.niddk.nih.gov/bax/nmrserver/pdbutil). An in-house code was used to graft the side chains to the backbone to synthesize the initial peptide structure. The peptide was prepared as a zwitterion, and the terminal benzimidazole groups' protonated, such that the peptide carries a net formal charge of (+20). The peptide was placed in a 9×9×9 nm cubic simulation box with periodic boundary conditions, and solvated by SPC water molecules to a density of 1.0 g/cm$^3$ along with 20 Cl$^-$ counter ions such that the system carried no net charge. The size of the simulation box was specified such that with a 1.2 nm real-space cutoff each solvent molecule was able to interact with at most one periodic image of the peptide, even in its fully extended conformation.

Molecular dynamics simulations were conducted using the GROMACS 4.6 simulation suite (Hess et al. (2008) J Chem Theory Comput 4(3):435-447). High-energy overlaps in the initial configuration were eliminated by steepest descent energy minimization to remove forces exceeding 1000 kJ/mol·nm. Simulations were performed in the NPT ensemble at 298 K and 1 bar, employing a Nose-Hoover thermostat and Parrinello-Rahman barostat. Initial atom velocities were randomly assigned from a Maxwell distribution at 298 K. The equations of motion were numerically integrated using a leap-frog algorithm with a 2 fs time step, and bond lengths fixed using the LINCS algorithm to improve efficiency. Electrostatic interactions were treated using Particle Mesh Ewald (PME) with a real-space cutoff of 1.2 nm and a 0.12 nm Fourier grid spacing. Lennard-Jones interactions were shifted smoothly to zero at a 1.2 nm, and Lorentz-Berthelot combining rules used to determine interaction parameters between unlike atoms. A 1.5 ns equilibration run was conducted, at which time the temperature, pressure, energy, and peptide radius of gyration had attained stable values. We then performed a 68 ns production run, harvesting snapshots of the system configuration for analysis every 5 ps. The peptide remained fully alpha-helical over the entire course of the simulation trajectory.

Minimal Inhibition Concentration (MIC).

Gram-negative bacteria, DH5a (E. coli), MG1655 (E. coli), C101 (Pseudomonas aeruginosa), and Gram-positive bacteria, ATCC12608 (S. aureus), ATCC11778 (Bacillus toyonensis), and methicillin-resistant S. aureus (MRSA) strains, NRS382, NRS383, NRS384 were grown in LB medium at 37° C. Clinical isolated Helicobacter pylori strains, B107, J291, J99, J99-AF, J99-A9 and J99-A11 were incubated in BB with 10% FBS supplemented with vancomycin (5 µg/mL) at 37° C. Among them, J99-AF, J99-A9 and J99-A11 are drug resistant bacteria. For determination of the MIC, polypeptides were dissolved in media using serial dilutions from a stock solution. Into each well of a 96-well plate was added 200 µL of each concentration and 2 µL of bacteria (1×10$^8$ CFU (colony forming units)) in medium. The plate was incubated at 37° C. The optical density readings of microorganism solutions were measured after 24 h incubation. The MIC was considered as the lowest concentration of peptide where no visual growth of bacteria was detected.

The stability of polypeptide was tested in the MIC assay in different environments, including salts, serum, plasma, tear fluid, and mucin. 1×10$^6$ CFU/ml of E. coli DH5a and S. aureus ATCC12608 were treated with peptides, while different conditions were added to LB medium, and the final concentrations of physiological conditions were as follows: 150 mM NaCl, 1 mM MgCl$_2$, 2.5 mM CaCl$_2$, 2% human serum, 5% FBS, 10% FBS, 2% plasma, 5% plasma, 2% artificial tear (from Boss Safety Products) and 1 mg/mL mucin. After these treatments, the procedures were same as the MIC assay described above.

Killing Kinetics.

The killing kinetics and killing efficiency of the AMPs such as PHLG-BIm were measured against the microbes by counting the colony forming units of live bacteria with agar plating. The bacteria were prepared using the same procedure described in the MIC measurement. The samples were treated with AMPs (e.g., PHLG-BIm$_{40}$) at MIC or double of the MIC and incubated at 37° C. under constant shaking (100 rpm). Samples were taken for a series of ten-fold dilutions, and plated out in LB agar plates at predetermined time intervals (1 h, 2 h, 8 h and 24 h). The plates were incubated over night at 37° C. and the bacteria were counted by CFU. The bacteria (DH5α, ATCC12608) were also incubated with AMPs at various concentrations without or with NaCl (150 mM), 2% human serum, 2% plasma, 2% artificial tear. The bacteria were prepared using the same procedure described in the MIC measurement. After 8 h incubation, samples were taken for a series of ten-fold dilutions, and plated out in LB agar plates, and the bacteria were counted by CFU after overnight incubation at 37° C.

Hemolytic Assay.

Fresh rabbit blood was obtained and subjected to 25-fold dilution with PBS buffer to reach a concentration of approximately 4% (in volume) of the blood cells. 300 µL of PBS solution containing a polymer at various concentrations was placed in a 1.5 mL microfuge tube, followed by the addition of an equal volume (300 µL) of red blood cell suspension. The mixture was incubated at 37° C. for 1 h to allow for the hemolysis process to take place. At the end of the incubation time, the non-hemolysed red blood cells were separated by centrifugation at 1000 rpm for 5 min. Aliquots (100 µL) of the supernatant were transferred to a 96-well plate, and hemoglobin release was measured by UV-absorbance at 576 nm using a microplate reader (TECAN, Switzerland). Two controls were provided in this assay: an untreated red blood cell suspension in PBS solution was used as the negative control; a solution containing red blood cells lysed with 1% Triton-X was used as the positive control. Percentage of hemolysis was calculated using the following formula: Hemolysis (%)=[(O.D. 576 nm of the treated sample−O.D. 576 nm of the negative control)/(O.D. 576 nm of positive control−O.D. 576 nm of negative control)]×100%.

The Stability of Polypeptides Against Protease.

PHLG-BIm (1.0 mg/mL) was incubated with trypsin (1.0 mg/mL) or pronase (0.12 mg/mL) or *Pseudomonas Aeruginosa* elastase (6.25 mg/L) in Tris buffer (pH 7.4) at 37° C. PHLG-BIm (1.0 mg/mL) was incubated with elastase from human leukocytes (25 mg/L) in sodium acetate buffer (0.05 M, pH 5.5, with 0.6 M NaCl) at 37° C. As a positive control, LL-37 (0.1 mg/mL) was also incubated with trypsin (0.1 mg/mL) or pronase (12 mg/L) or *Pseudomonas Aeruginosa* elastase (0.6 mg/L) in Tris buffer (pH 7.4) at 37° C. LL-37 (0.1 mg/mL) was incubated with elastase from human leukocytes (2.5 mg/L) in sodium acetate buffer at 37° C. After 8 h of incubation, the samples were taken out for HPLC analyses. In a separate experiment, PHLG-BIm (1.0 mg/mL) was incubated with trypsin (1.0 mg/mL) or pronase (0.12 mg/mL) in Tris buffer (pH 7.4) at 37° C. for 8 h and MIC measurement was conducted.

Flow Cytometry Analysis of Pore-Forming Activities.

For membrane permeability assay, $1\times10^6$ CFU MG1655 cells were combined with propidium iodide (PI) (final concentration 25 µM), HEPES (1 mM), glucose (1 mM) and polypeptide, and incubated for 15 min at room temperature. Changes in cell-associated dye fluorescence were measured with a BD Biosciences LSR II flow cytometer, using excitation at 488 nm with an argon laser and measurement of emission through a band-pass filter at 695/40 nm for PI. A minimum of 25,000 events were detected for each sample. Calculation the geometric mean fluorescence intensity (MFI) of each population was performed using FCS Express 3.00.0311 V Lite Stand-alone software.

Fluorescence Microscopy of Stained Bacterial Cells.

A Zeiss XBO 75 Fluorescence Microscope (Carl Zeiss) was used for fluorescence studies. A BacLight™ Kit L-7012 was used as the fluorescence dye in a mixture of propidium iodide:SYTO9 to examine bacteria in the presence of polypeptides. An initial bacterial concentration of ~$10^8$ cells/mL was used for microscopy for ease of visualization. The dye mixture was incubated with the bacteria at room temperature for 15 min prior to the addition of polypeptide solution. Solution of cells, dye, and polymer were allowed to stand for 30 min, and 50 µL of the solution was placed on a slide, mounted with a coverslip, and visualized under fluorescence microscope. Bacteria were viewed under a green filter (excitation/emission, 420-480 nm/520-800 nm) or a red filter (480-550 nm/590-800 nm).

Liposome Dye Leakage Assay.

Calcein dye was dissolved in Tris buffer (pH=7) to achieve a concentration of 40 mM. To a clean round-bottom flask, appropriate volumes of lipid stocks were added to make up 1 mL of $CHCl_3$. For 3:1 POPE (1-palmitoyl-2-oleoyl-sn-glycero-3-phosphoethanolamine)/POPG (1-palmitoyl-2-oleoyl-sn-glycero-3-phospho-(1'-rac-glycerol) (sodium salt)) vesicles, POPE (130 µL, 25 mg/mL $CHCl_3$) and POPG (115 µL, 10 mg/mL $CHCl_3$) were used. For DOPC (1,2-di-(9Z-octadecenoyl)-sn-glycero-3-phos- phocholine)/POPC (1-palmitoyl-2-oleoyl-sn-glycero-3-phosphocholine) vesicles, DOPC (100 µL, 25 mg/mL $CHCl_3$) and POPC (1 mL, 10 mg/mL $CHCl_3$) were used. The solvent was removed by a stream of nitrogen gas to obtain a thin lipid film, which was then hydrated by 1 mL of calcein solution. The mixture was left to stir for 1 h, after which it was subjected to 10 freeze-thaw cycles (using dry ice/acetone to freeze and warm water to thaw). The suspension was extruded 20 times through a polycarbonate membrane with 400 nm pore diameter. The excess dye was removed using Sephadex G-50 column as the eluent. The dye-filled vesicle fractions were diluted 200 times with Tris buffer. This suspension (90 µL) was subsequently mixed with polypeptide stock solutions (10 µL) on a 96-well black microplate (Greiner, flat bottom). Tris buffer (10 µL) and Triton-X (0.1% v/v, 10 µL) were employed as the negative and positive controls, respectively. After 30 min, the fluorescence intensity in each well was recorded using the microplate reader with excitation and emission wavelengths of 490 and 515 nm, respectively. The percentage of leaked calcein dye in each well was determined as follows: leakage (%)=[(F−$F_0$)/($F_{TX}$−$F_0$)]×100%, where F is the fluorescence intensity recorded in the well, $F_0$ is the intensity in the negative control well, and $F_{TX}$ is the intensity in the positive control well.

SEM Analysis.

MG1655 bacterial cells grown in LB with or without polypeptides treatment were performed using a similar protocol as MIC measurements but with a 30 min incubation time. All the samples were collected into a microfuge tube and pelleted at 4000 rpm for 5 min, and then washed twice with phosphate-buffered saline. Subsequently, bacteria were fixed with paraformaldehyde solution (4%) for 1 h before proceeding, followed by washing with DI water. Dehydration was performed with a series of graded ethanol solution (10%, 25%, 50%, 75%, 95%, and 100%). The dehydrated samples were dried under vacuum overnight before being mounted on carbon tape and coated with gold-platinum for imaging using a Hitachi S-4700 High Solution SEM (Japan).

Liposome Preparation for X-Ray Measurements.

DOPS (1,2-dioleoyl-sn-glycero-3-phospho-L-serine (sodium salt)), DOPE (1,2-dioleoyl-sn-glycero-3-phosphoethanolamine), DOPC (1,2-dioleoyl-sn-glycero-3-phosphocholine), DOPG (1,2-dioleoyl-sn-glycero-3-[phospho-rac-(1-glycerol)] (sodium salt)), and CL (bovine heart cardiolipin (sodium salt)), lyophilized lipids from Avanti Polar Lipids, were used without further purification to form small unilamellar vesicles (SUVs). Individual lipid stock solutions of DOPS, DOPE, DOPC, DOPG, and CL were prepared in chloroform at a concentration of 20 mg/mL. Mixtures of these lipids were prepared at molar ratios to yield each model membrane composition. The lipid solution mixtures were placed under $N_2$ to evaporate chloroform, and were further dried by overnight desiccation under vacuum. The dried lipid mixtures were solubilized the following day in 100 mM NaCl, 10 mM HEPES at pH 7.4 to a concentration of 20 mg/mL. These aqueous lipid solutions were incubated at 37° C. overnight and then sonicated until clear. SUVs were obtained by extrusion of sonicated lipid solution through a 0.2 µm pore Nucleopore filter (Whatman).

Small-Angle X-Ray Scattering Experiments.

Polypeptide and SUVs were mixed at specific P/L molar ratios. Samples were prepared in 100 mM NaCl, 10 mM HEPES at pH 7.4 and hermetically sealed in quartz capillaries (Hilgenberg GmbH, Mark-tubes). Small-angle X-ray scattering (SAXS) experiments were conducted at the Stanford Synchrotron Radiation Light source (SSRL, BL 4-2)

using monochromatic X-rays with an energy of 9 keV. The scattered radiation was collected using a Rayonix MX225-HE detector (pixel size of 73.2 μm). No radiation damage was observed for the incident beam intensities and the exposure times used. 2D SAXS powder patterns were integrated using the Nika 1.50 package for Igor Pro 6.21 and FIT2D.

SAXS Data Fits.

Q positions of the diffraction peaks were obtained by visual inspection of the integrated I(Q) vs. Q SAXS data graphed in Origin Lab software. The ratios between the measured peak positions ($Q_{(hkl)meas}$) were compared with those of permitted reflections for different crystal phases to determine the phases present in each sample. After identifying each crystal phase, a linear regression was fit through the set of points corresponding to the reflections, with each of these points having coordinates of its Q-position, $Q_{(hkl)meas}$, and the associated reflection in terms of Miller indices, h, k, l. For a powder-averaged cubic phase, $Q_{(hkl)meas}=(2\pi/a)\sqrt{(h^2+k^2+l^2)}$. As such, with a linear regression of $Q_{(hkl)meas}$ vs. $\sqrt{(h^2+k^2+l^2)}$ for cubic phases, we can calculate the cubic lattice parameter from the slope (m=2π/a).

The intracellular uptake of rifampicin. Bacterial strains MG1655 and C101 (1×10⁶ CFU) were incubated with rifampicin (4.85 μM and 38.9 respectively) without polypeptide or with PHLG-BIm₄₀ (3.3 μM) or with PHDLG-BIm₄₀ (3.3 After 0.5 h or 1 h incubation, the supernatant was obtained by filtration through 0.2 μm membrane and used for HPLC analysis.

Example 3. Antibacterial PHLG-Based Polypeptides

Peptides that adopt helical conformations have attracted much interesting due to their utility in medicine and biotechnology. A variety of natural antimicrobial peptides (AMPs) such as cecropins, magainins and melittin, possess amphipathic α-helix structure upon association with lipid bilayers. The amphipathic α-helix of AMPs correlates with their membrane activity and serves as a membrane-destabilizing agent, allowing insertion of hydrophobic components into membrane lipid domains to disrupt membrane structure when they interact with bacterial membranes. The membrane physical disruption mechanism of AMPs reduces the likelihood of pathogens developing resistance. However, the AMPs require precise sequence control to be active toward bacterial cell membranes.

We have reported methods for the facile generation of cationic and helical polypeptides (Lu, H.; Zhang, Y.; Cheng, J. *Nat. Commun.* 2011, 2, 206). The helical structure of cationic polypeptides can be stabilized by increasing the distance between the charged groups of the side chains and the backbone of the polypeptide, thus minimizing the effect of charge repulsion by reducing the charge density on the helix surface. Described in this example is a class of α-helical polypeptide AMP mimics that features long, hydrophobic side chains, each bearing a quaternary ammonium end group with distinct cationic chemical functionality (Scheme 3-1).

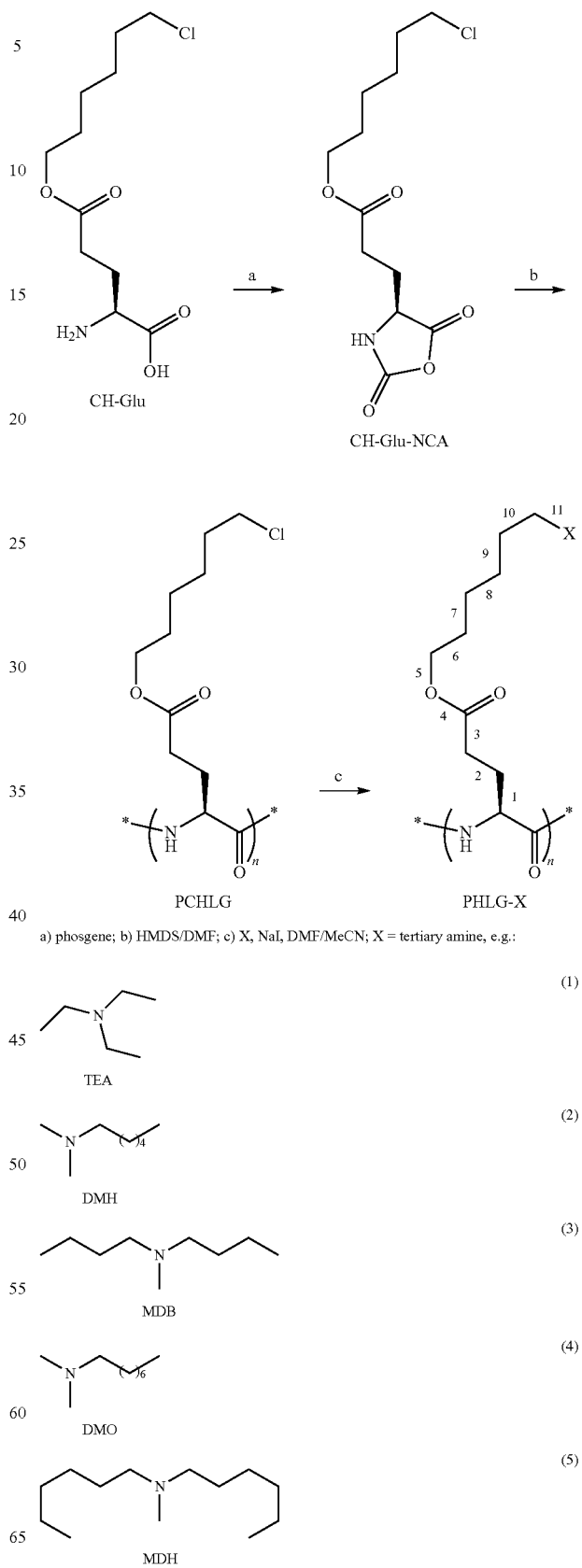

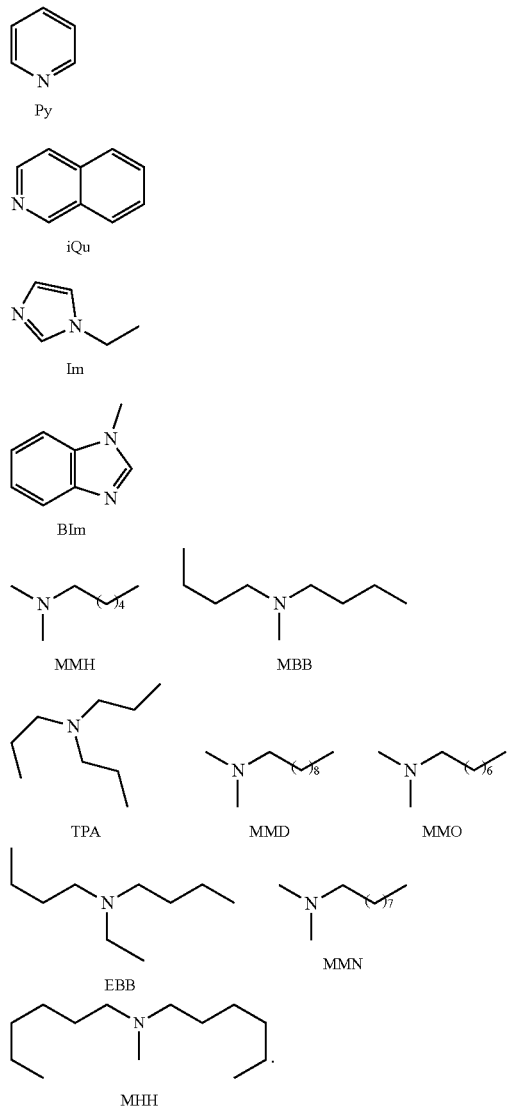

In various embodiments, X can be any suitable tertiary amine that forms a cation when covalently bonded to PCHLG to provide PHLG-X.

The long side chains (preferably 11-13 sigma bonds from the polymer backbone) extend the cationic ammonium groups away from the peptide back-bone, allowing for a more stable helical structure by reducing end group charge repulsion and increasing hydrophobic interactions between side chains. Unlike typical AMPS, which are characterized by charged and hydrophobic faces along an amphipathic helix, and random antimicrobial polymers, these polypeptides feature a rod-like, helical structure with a charged exterior "coat" and hydrophobic interior, where the hydrophobic interior of the helical polypeptide is shielded by the positively charged exterior "coat" to reduce hemolytic activity (FIG. 1B).

Also due to the helical structure, the polypeptides are able to present the positive charges in a well-organized manner to achieve an appropriate charge density that matches that of cell membranes and allows for efficient binding/interaction. The helical structure can significantly inhibit proteolysis due to the steric hindrance encountered from long, hydrophobic side chains having quaternary ammonium end groups. We demonstrate that their properties can be tailored to yield excellent antimicrobial activity against both Gram-negative and Gram-positive bacteria. We further show that the bacteria-killing ability of the polypeptides can be attributed to their ability to directly disrupt and permeabilize cell membrane. Accordingly, we find that these polypeptides can potentially enhance the potency of traditional antibiotics when administered together, by facilitating membrane penetration and up-take.

The monomer γ-chloroalkyl-L/DL-glutamic acid-based N-carboxylanhydrides (CH-L/DL-glu-NCA) was prepared via the monoesterification of corresponding glutamic acid and the subsequent cyclization reaction using phosgene (Scheme 3-1). The molecular structures of CH-L-glu-NCA and CH-DL-glu-NCA were confirmed by $^1$H NMR and $^{13}$C NMR. The polypeptides were then synthesized by controlled ring-opening polymerization of the CH-L/DL-Glu-NCA monomer initiated by hexamethyldisilazane in glovebox at room temperature (~22° C.). These polypeptides with chloroalkyl side-chains were then modified via nucleophilic reaction by tertiary amine-, imidazole-, or pyridine-based nucleophiles, generating quaternary ammonium, imidazolium, or pyridinium-based polypeptides, respectively (Scheme 3-1).

With a separation of 11-13 σ-bonds between the backbone and positive charges, the poly(L-glutamate)-based polypeptides were able to adopt stable α-helical conformations, which was verified by the two-minima CD curve at 208 and 222 nm (FIG. 9). Corresponding non-helical polypeptides were also synthesized through the polymerization of DL-conformation NCA to study the effect of helical structure on the antibacterial activity of polypeptides. The racemic poly(DL-glutamate) polypeptides showed no Cotton effects in their CD spectra (FIG. 9), consistent with their expected random conformation.

We investigated how the chemical and structural characteristics of the polypeptides affect their antimicrobial activity using minimal inhibitory concentration (MIC) and microbicidal assays. MIC is commonly used to assess the activity of antimicrobial agents, and is generally defined as the minimum concentration of an antimicrobial agent at which no visible bacteria growth is observed. We first determined the MICs of a range of helical polypeptides, PHLG-X (X=TEA, DMH, MDB, DMO, MDH), with 6, 8, 9, 10, 13 carbons on the R group, respectively, against Gram-negative bacteria DH5α (Escherichia coli). As the of number of carbons on R group increased, the polypeptides with a more hydrophobic end group were found to have lower MIC values and also lower HC50 value (HC50=50% hemolytic concentration). This is consistent with previous findings correlating high hydrophobicity with increased overall toxicity. The polypeptides showed very low hemolytic activity when the number of carbon on R group less than 9. When the number of carbons on R group was more than 9, the hemolytic activity was remarkably increased while the antibacterial activity increased little if at all. As a result, PHLG-DMH and PHLG-DMO, with 9 and 10 carbons on the R groups, showed the highest selectivity against DH5α, with >32 and 64 times selectivity, respectively. The same phenomenon was found in Gram-negative bacteria MG1655 (E. coli), and Gram-positive bacteria, ATCC12608 (Staphylococcus aureus), and ATCC11778 (Bacillus toyonensis) (Table 3-1).

TABLE 3-1

The antibacterial activity and hemolytic activity of polypeptides against bacteria including MG1655 (E. coli), ATCC12608 (Staphylococcus aureus), and ATCC11778 (Bacillus toyonensis).

| Polypeptides | Number of carbon on R group | LogP of N-R group | Longest chain on R group | MIC (μM) DH5α (Selectivity[a]) | MG1655 (Selectivity[a]) | ATCC12608 (Selectivity[a]) | ATCC 11778 (Selectivity[a]) | HC50 (μM) |
|---|---|---|---|---|---|---|---|---|
| PHLG-MMH | 8 | 2.32 | 6 | 13.3 (>8) | 53.2 (>2) | >106.3 (<1) | 106.3 (>1) | >106.3 |
| PHLG-PPP | 9 | 2.72 | 3 | 6.4 (>16) | 51.2 (>2) | 51.2 (>2) | 12.8 (>8) | >102.5 |
| PHLG-MBB | 9 | 2.73 | 4 | 3.2 (>32) | 12.8 (>8) | 12.8 (>8) | 3.2 (>32) | >102 |
| PHLG-EBB | 10 | 3.06 | 4 | 1.4 (>64) | 5.8 (>16) | 11.6 (>8) | 2.9 (>32) | >93.2 |
| PHLG-MMO | 10 | 3.15 | 8 | 0.4 (64) | 1.5 (16) | 6.2 (4) | 3.1 (8) | 24.7 |
| PHLG-MMN | 11 | 3.57 | 9 | 0.7 (8) | 1.4 (4) | 0.4 (16) | 0.7 (8) | 5.6 |
| PHLG-BBB | 12 | 3.97 | 4 | 0.7 (>128) | 2.7 (>32) | 1.4 (>64) | 1.4 (>64) | >87.5 |
| PHLG-MMD | 12 | 3.99 | 10 | 1.4 (4) | 2.7 (2) | 0.7 (8) | 0.3 (16) | 5.5 |
| PHLG-MHH | 13 | 4.4 | 6 | 0.3 (8) | 1.4 (2) | 0.3 (8) | 0.3 (8) | 2.8 |

[a]Selectivity is defined as HC50/MIC.

When compared to their non-helical polypeptides, the helical PHLG-DMH and PHLG-DMO peptides exhibited much higher antibacterial activity and slightly higher hemolytic activity to all bacterial cells, showing higher selectivity against bacteria. This can be attributed to the condensed, rod-like helical structures, which are able to present the positive charges in a well-organized manner to achieve the appropriate charge density to match that of bacterial cell membranes and allow for efficient binding/interaction, while the hydrophobic part of the helical polypeptides is shielded by the positive charged exterior "coat".

We also studied the effect of aromatic R group on the antibacterial activity and hemolytic activity. Helical polypeptides PHLG-X (Py, iQu, Im, and BIm) and corresponding non-helical polypeptides were synthesized. The secondary structure of the polypeptides was demonstrated by CD spectra (FIGS. 10a and 10b). Again, the polypeptides with a more hydrophobic aromatic R group were found to have lower MIC values (Table 3-2), indicating higher antibacterial activity.

For example, PHLG-BIm had MIC values of 100, 400, 200 and 200 mg/L against DH5α, MG1655, ATCC12608, and ATCC11778, which were all significantly lower than those of PHLG-Im. Also, the helical PHLG-X peptides exhibited higher antibacterial activity and slightly higher hemolytic activity compared to their non-helical PHDLG-X counter-parts. PHLG-BIm had MIC values 8, 4, 4 and 4 times lower than those of PHDLG-BIm against DH5α, MG1655, ATCC12608, and ATCC11778, respectively. Although the helical PHLG-X polypeptides exhibited slightly lower HC50 than their corresponding non-helical analogues, their selectivity consistently exceeded that of the non-helical polypeptides. The microbicidal activity of the helical polypeptides was confirmed using colony assays, in which bacteria were incubated with a representative polypeptide, PHLG-BIm. Results showed early 100% killing of all five bacteria at their respective MIC or double MIC within 2 hours (FIG. 6).

We also discovered that antimicrobial activity could be increase by adding hydrophobic aliphatic chains at one end of the polypeptides, for example, by initiating the ring-opening polymerization with a $(C_1-C_{60})$alkylamine, as shown below in Scheme 3-2.

TABLE 3-2

The antibacterial activity and hemolytic activity of polypeptides against DH5α, MG1655, ATCC12608, and ATCC11778.

| Polypeptides | MIC (mg/L) DH5α (Selectivity[a]) | MG1655 (Selectivity[a]) | ATCC12608 (Selectivity[a]) | ATCC 11778 (Selectivity[a]) | HC50 (mg/L) |
|---|---|---|---|---|---|
| PHLG-Py | 200 (>8) | 400 (>4) | >1600 (<1) | 1600 (>1) | >1600 |
| PHDLG-Py | >1600 (<1) | >1600 (<1) | >1600 (<1) | >1600 (<1) | >1600 |
| PHLG-iQu | 200 (4) | 200 (4) | 200 (4) | 100 (8) | 800 |
| PHDLG-iQu | 400 (>4) | 800 (>2) | 800 (>2) | 400 (>4) | >1600 |
| PHLG-Im | 400 (>4) | 800 (>2) | >1600 (<1) | 1600 (>1) | >1600 |
| PHDLG-Im | >1600 (<1) | >1600 (<1) | >1600 (<1) | >1600 (<1) | >1600 |
| PHLG-BIm | 100 (>16) | 400 (>4) | 200 (>8) | 200 (>8) | >1600 |
| PHDLG-BIm | 800 (>2) | 1600 (>1) | 800 (>2) | 800 (>2) | >1600 |

[a]Selectivity is defined as HC50/MIC.

Scheme 3-2. Preparation of Antimicrobial Polypeptides Having Terminal Aliphatic Groups

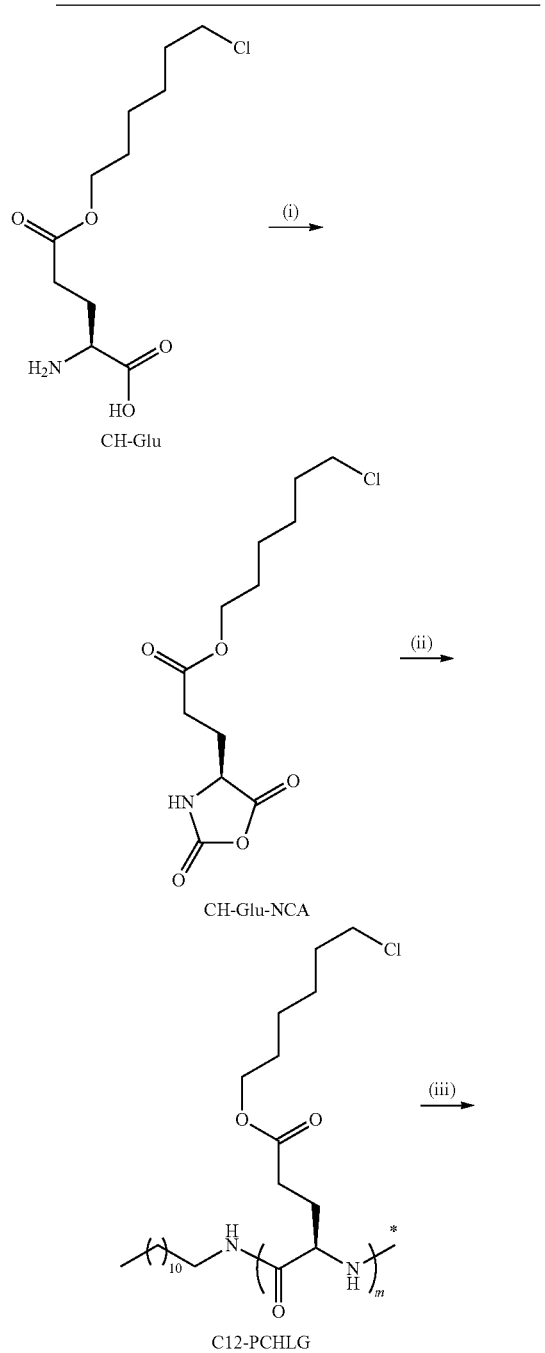

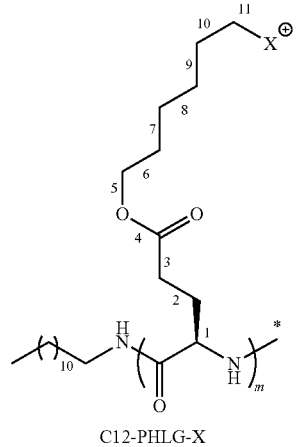

(i) phosgene; (ii) N—TMS—(C$_1$-C$_{60}$)alkylamine (e.g., N—TMS-dodecanamine)/DMF; iii) X, NaI, DMF/MeCN; X = tertiary amine In Scheme 3-2, X can be any suitable tertiary amine such as those illustrated above for Scheme 3-1. Specific useful examples include MBB (methyl dibutyl amine), EBB (ethyl dibutyl amine), and TPA (tripropyl amine). Useful ROP initiators include (C$_1$-C$_{60}$)alkylamines that have a suitable silane attached to the amine. The (C$_1$-C$_{60}$)alkyl can be a (C$_4$-C$_{60}$)alkyl, and can be straight chain or branched. Examples include:

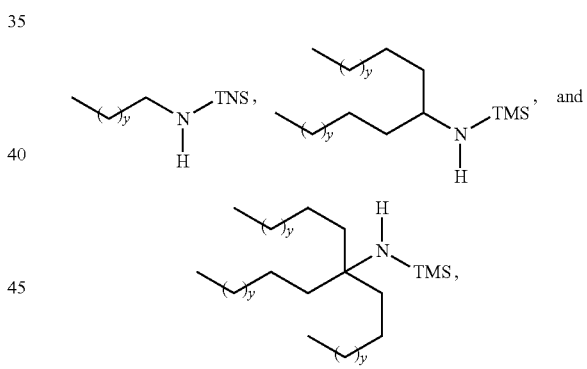

where y is 0 to about 16.

Initiation of the ring-opening polymerization with N-TMS-dodecanamine thus provides C12-PHLG-X polymers, the analysis of which provided the data shown in Table 3-3.

TABLE 3-3

The antibacterial activity and hemolytic activity of polypeptides against DH5α, MG1655, ATCC12608, and ATCC11778.

| Polypeptide | MIC (mg/L) | | | | | | Hemolytic activity (HC50, mg/L) |
| | MG1655 | ATCC12608 | DH5α | ATCC11778 | USA 100 | USA 200 | |
| --- | --- | --- | --- | --- | --- | --- | --- |
| C12-PHLG10-MBB | 50 | 100 | 6.25 | 12.5 | 6.25 | 6.25 | 800 |
| C12-PHLG40-MBB | 50 | 50 | 50 | 50 | 25 | 50 | 3200 |

TABLE 3-3-continued

The antibacterial activity and hemolytic activity of polypeptides against DH5α, MG1655, ATCC12608, and ATCC11778.

| Polypeptide | MIC (mg/L) | | | | | | Hemolytic activity (HC50, mg/L) |
| --- | --- | --- | --- | --- | --- | --- | --- |
| | MG1655 | ATCC12608 | DH5α | ATCC11778 | USA 100 | USA 200 | |
| C12-PHLG10-TPA | 200 | 200 | 200 | 400 | 200 | 200 | 1600 |
| C12-PHLG40-EBB (poor solubility) | >400 | >400 | >400 | >400 | >400 | >400 | 3200 |

In conclusion, from rationally-designed helical cationic polypeptides, we demonstrated that the helical structure and side-chain arrangement can significantly enhance the antibacterial activity of polypeptides. The cationic polypeptides can effectively kill gram-positive and gram-negative bacteria and showed high pore-forming ability toward bacterial membranes, which further increased the permeability toward antibiotics and enhanced the antibacterial activity of commercial antibiotics. These antimicrobial polypeptides are promising as antimicrobial drugs for the treatment of various bacterial infectious diseases.

Example 4. Pharmaceutical Dosage Forms

The following formulations illustrate representative pharmaceutical dosage forms that may be used for the therapeutic or prophylactic administration of a compound (e.g., a peptide) of a formula described herein, a compound specifically disclosed herein, or a pharmaceutically acceptable salt or solvate thereof (hereinafter referred to as 'Compound X'):

| (i) Tablet 1 | mg/tablet |
| --- | --- |
| 'Compound X' | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
| --- | --- |
| 'Compound X' | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
| --- | --- |
| 'Compound X' | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/mL) | mg/mL |
| --- | --- |
| 'Compound X' (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/mL) | mg/mL |
| --- | --- |
| 'Compound X' (free acid form) | 10.0 |
| Monobasic sodium phosphate | 0.3 |
| Dibasic sodium phosphate | 1.1 |
| Polyethylene glycol 400 | 200.0 |
| 0.1N Sodium hydroxide solution (pH adjustment to 7.0-7.5) | q. s. |
| Water for injection | q.s. ad 1 mL |

| (vi) Aerosol | mg/can |
| --- | --- |
| 'Compound X' | 20 |
| Oleic acid | 10 |
| Trichloromonofluoromethane | 5,000 |
| Dichlorodifluoromethane | 10,000 |
| Dichlorotetrafluoroethane | 5,000 |

| (vii) Topical Gel 1 | wt. % |
| --- | --- |
| 'Compound X' | 5% |
| Carbomer 934 | 1.25% |
| Triethanolamine (pH adjustment to 5-7) | q.s. |
| Methyl paraben | 0.2% |
| Purified water | q.s. to 100 g |

| (viii) Topical Gel 2 | wt. % |
| --- | --- |
| 'Compound X' | 5% |
| Methylcellulose | 2% |
| Methyl paraben | 0.2% |
| Propyl paraben | 0.02% |
| Purified water | q.s. to 100 g |

| (ix) Topical Ointment | wt. % |
| --- | --- |
| 'Compound X' | 5% |
| Propylene glycol | 1% |

| (ix) Topical Ointment | wt. % |
|---|---|
| Anhydrous ointment base | 40% |
| Polysorbate 80 | 2% |
| Methyl paraben | 0.2% |
| Purified water | q.s. to 100 g |

| (x) Topical Cream 1 | wt. % |
|---|---|
| 'Compound X' | 5% |
| White bees wax | 10% |
| Liquid paraffin | 30% |
| Benzyl alcohol | 5% |
| Purified water | q.s. to 100 g |

| (xi) Topical Cream 2 | wt. % |
|---|---|
| 'Compound X' | 5% |
| Stearic acid | 10% |
| Glyceryl monostearate | 3% |
| Polyoxyethylene stearyl ether | 3% |
| Sorbitol | 5% |
| Isopropyl palmitate | 2% |
| Methyl Paraben | 0.2% |
| Purified water | q.s. to 100 g |

These formulations may be prepared by conventional procedures well known in the pharmaceutical art. It will be appreciated that the above pharmaceutical compositions may be varied according to well-known pharmaceutical techniques to accommodate differing amounts and types of active ingredient 'Compound X'. Aerosol formulation (vi) may be used in conjunction with a standard, metered dose aerosol dispenser. Additionally, the specific ingredients and proportions are for illustrative purposes. Ingredients may be exchanged for suitable equivalents and proportions may be varied, according to the desired properties of the dosage form of interest.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. A radially amphiphilic polymer consisting essentially of Formula II:

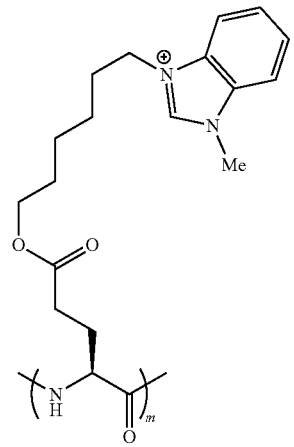

(II)

wherein m is about 6 to about 100; or a salt thereof.

2. A pharmaceutical composition comprising a polymer of claim 1 and a second antibiotic.

3. The pharmaceutical composition of claim 2 wherein the second antibiotic is an aminoglycoside, a tetracycline, or a beta-lactam.

4. The pharmaceutical composition of claim 3 wherein the second antibiotic is streptomycin, gentamicin, doxycycline, rifampicin, or penicillin.

5. The pharmaceutical composition of claim 2 further comprising a pharmaceutically acceptable diluent or carrier.

6. A method for inhibiting bacterial growth comprising contacting bacteria with the polymer of claim 1, under conditions sufficient to inhibit the growth of the bacteria.

7. The method of claim 6 wherein the bacteria are Gram-positive bacteria.

8. The method of claim 6 wherein the bacteria are Gram-negative bacteria.

9. The method of claim 6 further comprising contacting the bacteria with a second antibiotic.

10. A method of treating a bacterial infection in a mammal comprising administering to a mammal infected with a pathogenic bacterium an effective amount of the polymer of claim 1, thereby treating the bacterial infection by killing the bacteria, inhibiting the growth of the bacteria, or a combination thereof.

11. The method of claim 10 wherein the bacteria are Gram-positive bacteria.

12. The method of claim 10 wherein the bacteria are Gram-negative bacteria.

13. The method of claim 10 further comprising administering a second antibiotic, wherein the activity of the combination of the polymer and the second antibiotic is synergistic toward the bacterial infection.

14. The method of claim 10 wherein the ratio of hemolytic activity to antibacterial activity is at least 4 to 1.

* * * * *